United States Patent [19]
Hirschmann et al.

[11] Patent Number: 5,976,404
[45] Date of Patent: Nov. 2, 1999

[54] SUPERTWIST LIQUID-CRYSTAL DISPLAY

[75] Inventors: Harald Hirschmann; Clarissa Weller, both of Darmstadt; Volker Reiffenrath, Rossdorf, all of Germany

[73] Assignee: Merck Patent Gesellschaft mit Beschrankter Haftung, Germany

[21] Appl. No.: 08/980,350

[22] Filed: Nov. 28, 1997

[30] Foreign Application Priority Data

Nov. 30, 1996 [DE] Germany .................. 196 49 678

[51] Int. Cl.⁶ .................... C09K 19/52; C09K 19/30; C09K 19/20
[52] U.S. Cl. .................. 252/299.01; 252/299.61; 252/299.63; 252/299.66; 252/299.67
[58] Field of Search .............. 252/299.01, 299.63, 252/299.61, 299.64, 299.65, 299.66, 299.67

[56] References Cited

U.S. PATENT DOCUMENTS

| | | | |
|---|---|---|---|
| 5,308,538 | 5/1994 | Weber et al. | 252/299.61 |
| 5,374,374 | 12/1994 | Weber et al. | 252/299.63 |
| 5,387,369 | 2/1995 | Weber et al. | 252/299.01 |
| 5,516,454 | 5/1996 | Scheuble et al. | 252/299.01 |
| 5,702,640 | 12/1997 | Junge et al. | 252/299.01 |
| 5,714,087 | 2/1998 | Pausch et al. | 252/299.01 |

*Primary Examiner*—Shean C. Wu
*Attorney, Agent, or Firm*—Millen, White, Zelane & Branigan, P.C.

[57] ABSTRACT

Supertwist liquid-crystal displays having excellent properties are obtained if the nematic liquid-crystal mixture comprises at least one compound of the formula I

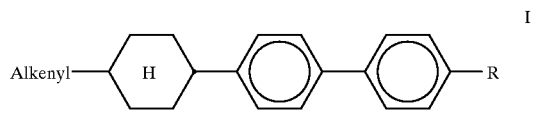

and at least one compound of the formula I'

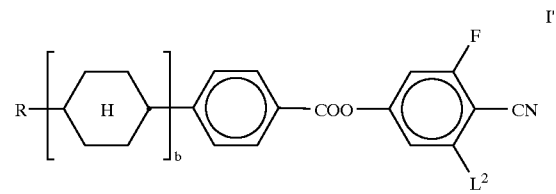

in which

Alkenyl is an alkenyl radical having 2 to 7 carbon atoms,

R is an alkyl group having 1 to 12 carbon atoms, in which, in addition, one or two non-adjacent $CH_2$ groups may be replaced by —O—, —CH=CH—, —CO—, —OCO— or —COO—, b is 0 or 1, and $L^2$ is H or F.

18 Claims, No Drawings

SUPERTWIST LIQUID-CRYSTAL DISPLAY

The invention relates to supertwist liquid-crystal displays (SLCD) having very short response times and good steepnesses and angle dependencies, and to the novel nematic liquid-crystal mixtures used therein.

BACKGROUND OF THE INVENTION

SLCDs are known, for example, from EP 0 131 216 B1; DE 34 23 993 A1; EP 0 098 070 A2; M. Schadt and F. Leenhouts, 17th Freiburg Congress on Liquid Crystals (8.-10.04.87); K. Kawasaki et al., SID 87 Digest 391 (20.6); M. Schadt and F. Leenhouts, SID 87 Digest 372 (20.1); K. Katoh et al., Japanese Journal of Applied Physics, Vol. 26, No. 11, L 1784-L 1786 (1987); F. Leenhouts et al., Appl. Phys. Lett. 50 (21), 1468 (1987); H. A. van Sprang and H. G. Koopman, J. Appl. Phys. 62 (5), 1734 (1987); T. J. Scheffer and J. Nehring, Appl. Phys. Lett. 45 (10), 1021 (1984), M. Schadt and F. Leenhouts, Appl. Phys. Lett. 50 (5), 236 (1987) and E. P. Raynes, Mol. Cryst. Liq. Cryst. Letters Vol. 4 (1), pp. 1–8 (1986). The term SLCD here covers any more highly twisted display element with a value for the twist angle of between 160° and 360°, such as, for example, the display elements of Waters et al. (C. M. Waters et al., Proc. Soc. Inf. Disp. (New York)(1985)(3rd Intern. Display Conference, Kobe, Japan), STN-LCDs (DE-A 35 03 259), SBE-LCDs (T. J. Scheffer and J. Nehring, Appl. Phys. Lett. 45 (1984) 1021), OMI-LCDs (M. Schadt and F. Leenhouts, Appl. Phys. Lett. 50 (1987), 236), DST-LCDs (EP-A 0 246 842) or BW-STN-LCDs (K. Kawasaki et al., SID 87 Digest 391 (20.6)).

SLCDs of this type are distinguished, in comparison to standard TN displays, by significantly better steepnesses of the electrooptical characteristic line and consequently better contrast values, and by significantly less angle dependence of the contrast. Of particular interest are SLCDs having very short response times, in particular also at relatively low temperatures. In order to achieve short response times, the viscosities, in particular, of the liquid-crystal mixtures were hitherto optimized using usually monotropic additives having relatively high vapor pressure. However, the response times achieved were not adequate for all applications.

In order to achieve a steep electrooptical characteristic line, the liquid-crystal mixtures should have relatively large values for $K_{33}/K_{11}$ and relatively small values for $\Delta\epsilon/\epsilon\perp$.

In addition to optimization of the contrast and the response times, further important requirements are made of mixtures of this type:

1. A broad d/p window
2. High long-term chemical stability
3. High electrical resistance
4. Low frequency dependence of the threshold voltage.

The parameter combinations achieved are still far from adequate, in particular for high-multiplex STNs (1/400). This is in some cases attributable to the fact that the various requirements are affected in opposite manners by material parameters.

There thus continues to be a great demand for SLCDs having very short response times and at the same time a large operating temperature range, high characteristic line steepness, good angle dependence of the contrast and low threshold voltage which meet the above-mentioned requirements.

SUMMARY OF THE INVENTION

The invention has an object of providing SLCDs which do not have the above-mentioned disadvantages, or only do so to a lesser extent, and at the same time have very good response times.

Upon further study of the specification and appended claims, further objects and advantages of this invention will become apparent to those skilled in the art.

It has now been found that this object can be achieved if nematic liquid-crystal mixtures are used which comprise at least one compound of the formula I

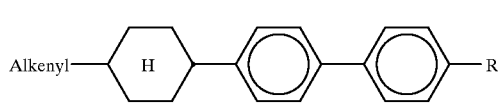

and at least one compound of the formula I'

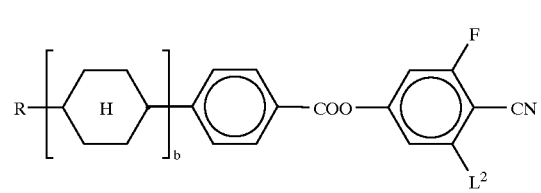

in which

Alkenyl is an alkenyl radical having 2 to 7 carbon atoms,

R is an alkyl group having 1 to 12 carbon atoms, in which, in addition, one or two non-adjacent $CH_2$ groups may be replaced by —O—, —CH=CH—, —CO—, —OCO— or —COO—, b is 0 or 1, and $L^2$ is H or F.

Mixtures comprising compounds of the formula I give lower rotational viscosities, lower threshold voltages, higher optical anisotropy values and significantly shorter response times than mixtures comprising 4'-substituted 4-(4-alkylcyclohexyl)-biphenyls, while having comparable clearing points and steepnesses.

The invention thus relates to an SLCD containing two plane-parallel outer plates which, together with a frame, form a cell, a nematic liquid-crystal mixture of positive dielectric anisotropy which is present in the cell, electrode layers with superposed alignment layers on the insides of the outer plates, a pitch angle between the longitudinal axis of the molecules at the surface of the outer plates and the outer plates of from about 1 degree to 30 degrees, and a twist angle of the liquid-crystal mixture in the cell from alignment layer to alignment layer with a value of between 100 and 600°, a nematic liquid-crystal mixture consisting of a) 10–65% by weight of a liquid-crystalline component A consisting of one or more compounds having a dielectric anisotropy of greater than +1.5;

b) 20–90% by weight of a liquid-crystalline component B consisting of one or more compounds having a dielectric anisotropy of between −1.5 and +1.5;

c) 0–20% by weight of a liquid-crystalline component D consisting of one or more compounds having a dielectric anisotropy of below −1.5, and d) an optically active component C in such an amount that the ratio between the layer thickness (separation of the plane-parallel outer plates) and the natural pitch of the chiral nematic liquid-crystal mixture is from about 0.2 to 1.3, characterized in that component B comprises at least one compound of the formula I

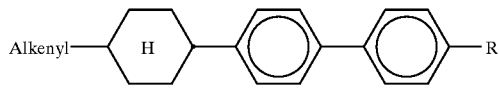

I and component A comprises at least one compound of the formula I'

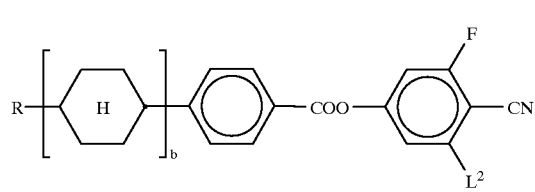

I' in which

Alkenyl is an alkenyl radical having 2 to 7 carbon atoms,

R is an alkyl group having 1 to 12 carbon atoms, in which, in addition, one or two non-adjacent $CH_2$ groups may be replaced by —O—, —CH=CH—, —CO—, —OCO— or —COO—, b is 0 or 1, and $L^2$ is H or F.

The invention also relates to corresponding liquid-crystal mixtures for use in SLCDS.

Preferred compounds of the formula I are in particular compounds of the subformulae IA and IB

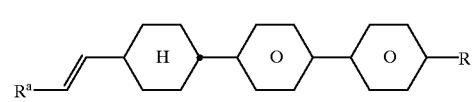

IA

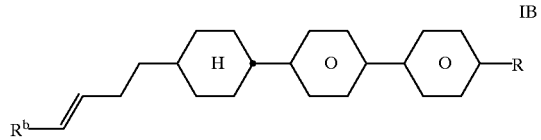

IB $R^a$ is preferably straight-chain alkyl having 1 to 5 carbon atoms.

$R^b$ is preferably straight-chain alkyl having 1 to 3 carbon atoms.

Preferred compounds of the formula I' are in particular the compounds of the subformulae I'A to I'C.

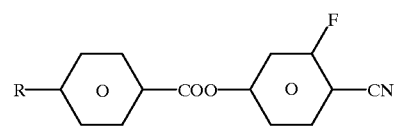

I'A

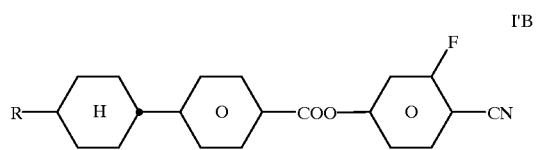

I'B

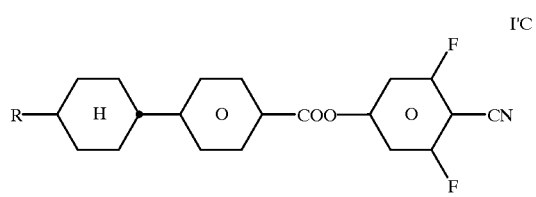

I'C

Particular preference is given to the compounds of the formula I'A, in which R is preferably straight-chain alkyl having 2 to 4 carbon atoms or alkenyl.

Component A preferably comprises compounds of the formulae II, II' or III

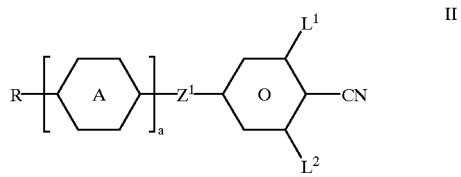

II

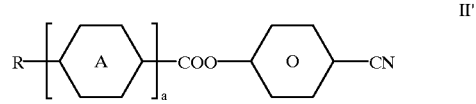

II'

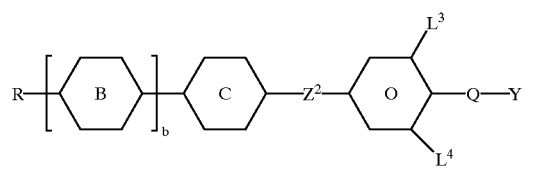

III in which

R is an alkyl group having 1 to 12 carbon atoms, in which, in addition, one or two non-adjacent $CH_2$ groups may also be replaced by —O—, —CH=CH—, —CO—, —OCO— or —COO—,

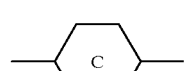

are each independently of one another

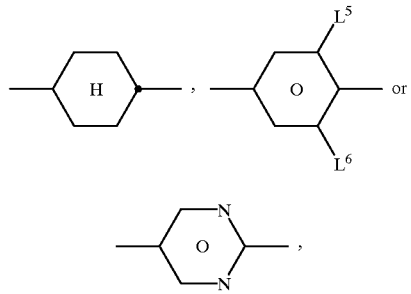

$L^{1-6}$ are each, independently of one another, H or F, $Z^1$ is —CH$_2$CH$_2$— or a single bond, $Z^2$ is —CH$_2$CH$_2$—, —COO—, —C≡C— or a single bond, Q is —CF$_2$—, —CHF—, —OCF$_2$—, —OCHF— or a single bond, Y is F or Cl, a is 1 or 2, and b is 0 or 1.

Preferred compounds of the formula II conform to the subformulae IIa to IIc:

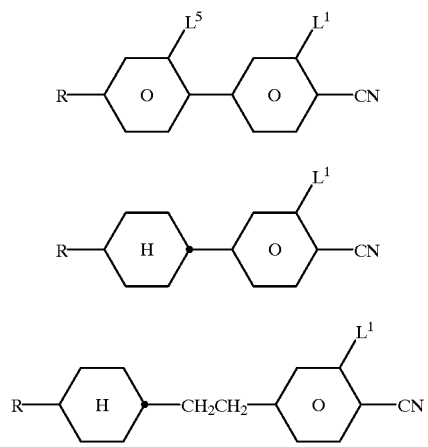

where R, $L^1$ and $L^5$ are as defined above.

Preferred compounds of the formula II' conform to the subformulae II'a and II'b

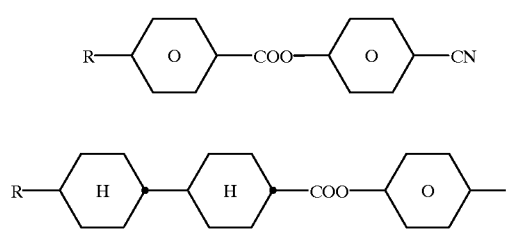

where

R is as defined above.

Component A furthermore preferably comprises the following compounds of the formula Z I to Z IV

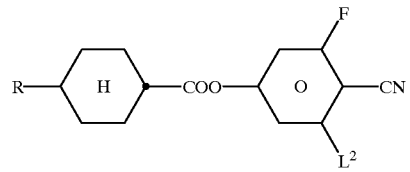

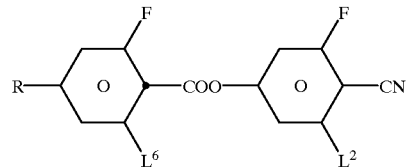

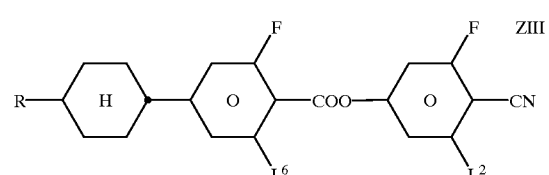

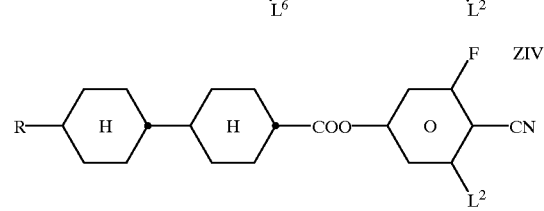

in which

R, $L^2$ and $L^6$ are as defined above.

Preferred compounds of the formula III conform to the subformulae IIIa—IIIr:

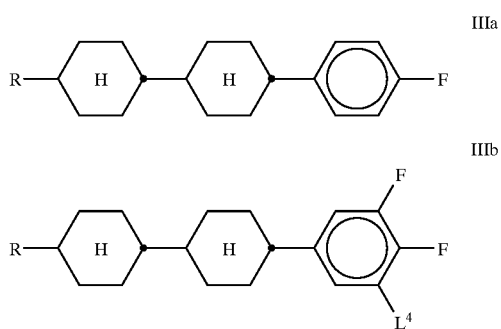

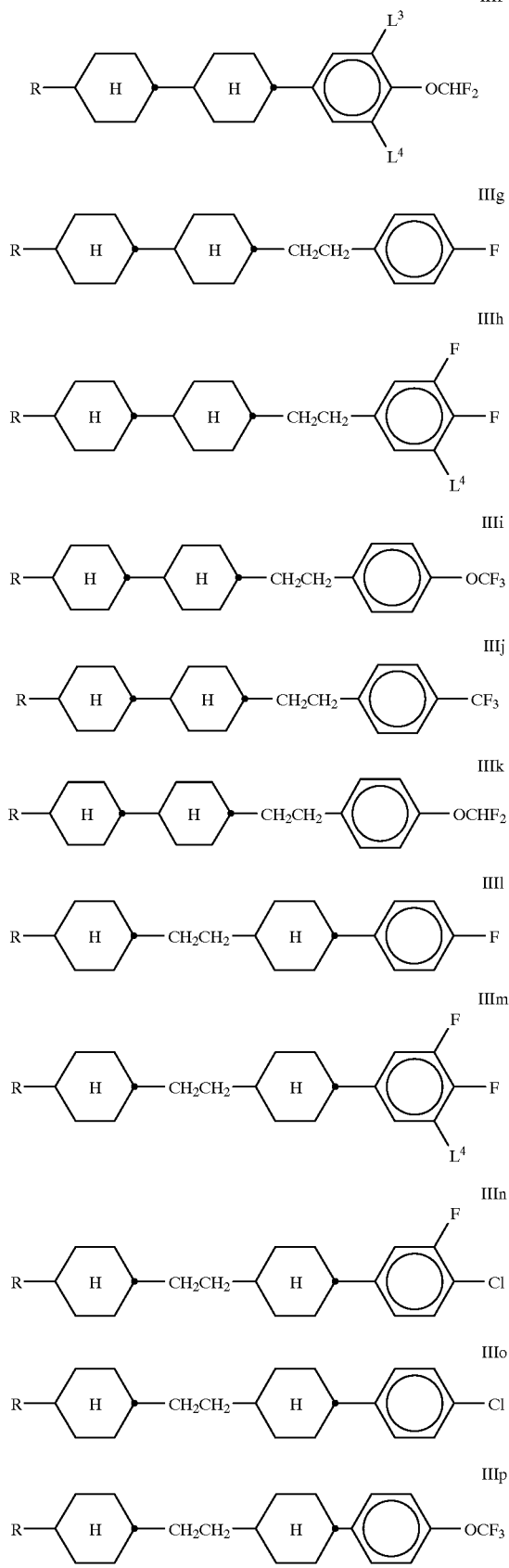

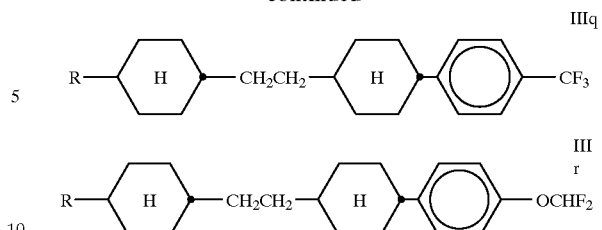

$L^3$ and $L^4$ are H or F.

In addition to one or more compounds of the formula I, preferred mixtures comprise one, two, three, or more compounds of the formulae IIa, IIb, IIc, II'a, IIId, IIIh, IIIi, IIIl, IIIm or IIIr, preferably one or more compounds of the formula IIId or IIIh, and one to four compounds of the formula I and one to three compounds of the formulae IIb and II'a.

R is preferably straight-chain alkyl or IE- or 3E-alkenyl having 1 to 5 carbon atoms.

The individual compounds, for example, of the formulae I, I', II, II' and III or their subformulae or alternatively other compounds which can be used in the novel SLCDs are either known or can be prepared analogously to the known compounds.

In a particularly preferred embodiment, component A additionally comprises compounds of the formulae AI to AVI: R

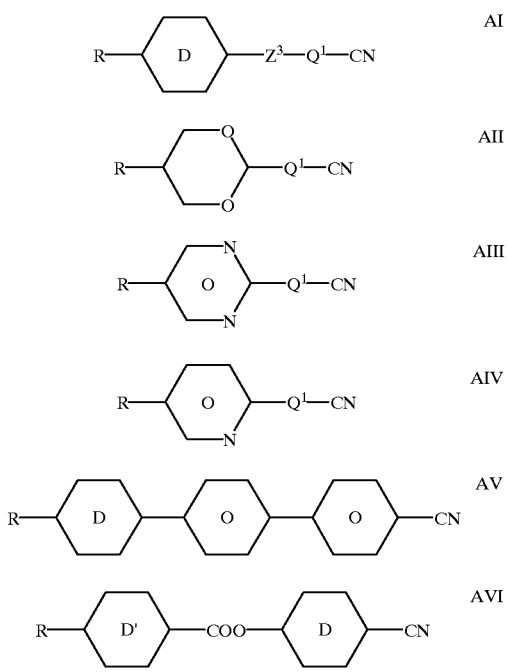

in which

R is an alkyl group having 1 to 12 carbon atoms, in which, in addition, one or two non-adjacent $CH_2$ groups may also be replaced by —O—, —CH=CH—, —CO—, —OCO— or —COO—, $Z^3$ is

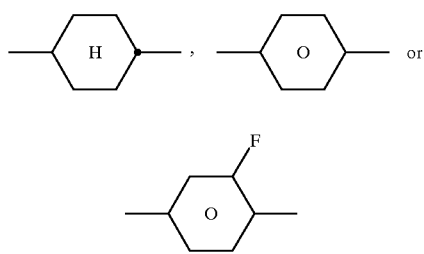

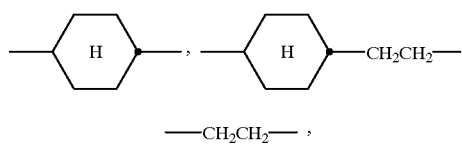

O—CO— or a single bond,

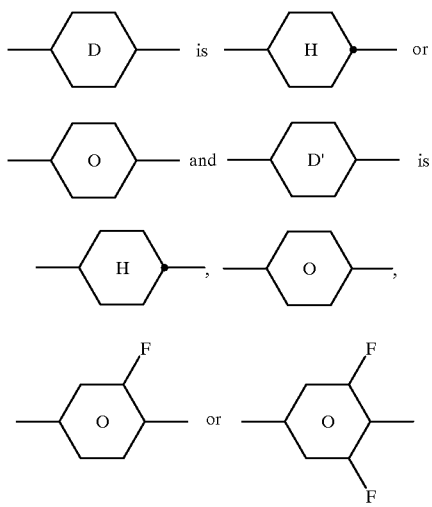

The mixtures preferably comprise from 5 to 50% of compounds of the formula AI and AVI. Preference is given to compounds of the formulae IIa1, IIb1, IIc1, IIa2, IIb2 and II'a:

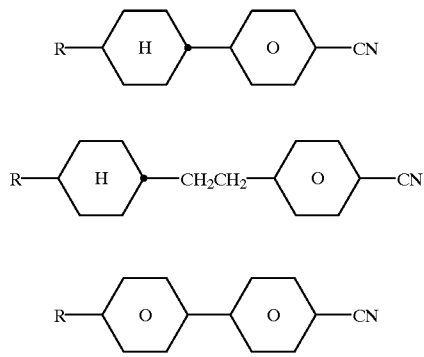

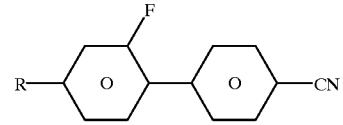

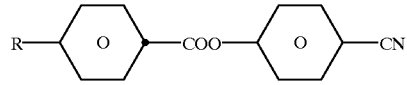

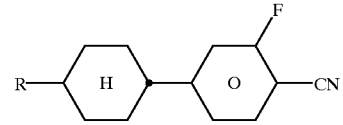

Component A preferably comprises one or more compounds of the formulae IIb1.

The novel mixtures preferably comprise one or more polar compounds having a high clearing point selected from the group consisting of the compounds IIe to IIh and II'b:

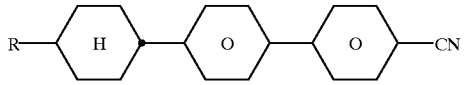

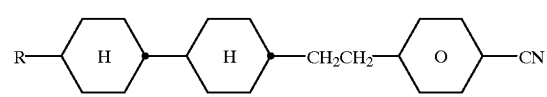

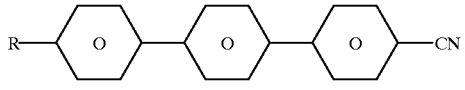

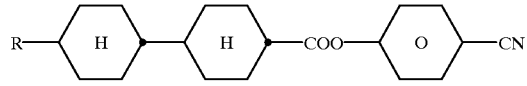

In the compounds IIe to IIh, the 1,4-phenylene rings can also be laterally substituted by one or two fluorine atoms. Preferred compounds of this type are the compounds of the formulae IIe1 to IIe3:

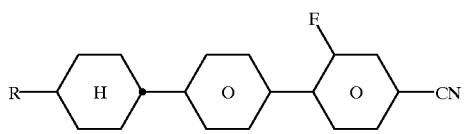

IIe2

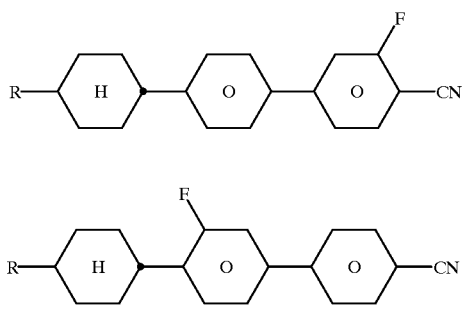

IIe3

In the novel mixtures, the proportion of compounds IIe to IIh and II'b is preferably from about 2 to 25%. Preferred liquid-crystal mixtures comprise one or more compounds from Group B, preferably 10 to 40%. The compounds from Group B are distinguished both by their low rotational viscosity ($y_1$) values of <150 mPa·s and by their high clearing point (>120° C.).

Component B comprises one or more compounds selected from the group consisting of the compounds of the formulae IV1 to IV8:

IV1
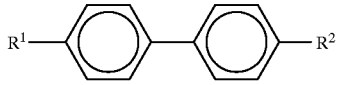

IV2
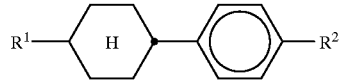

IV3
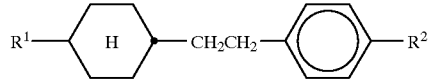

IV4
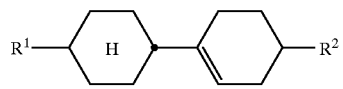

IV5
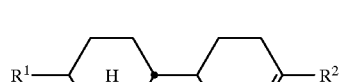

IV6
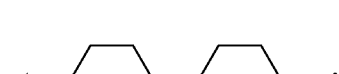

IV7

IV8

in which $R^1$ and $R^2$ are as defined for R.

Component B additionally comprises one or more compounds selected from the group consisting of the compounds of the formulae IV9 to IV21

IV9
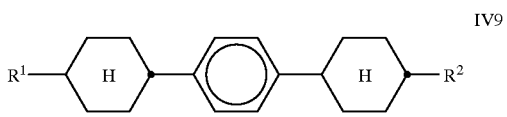

IV10
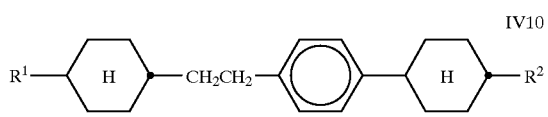

IV11
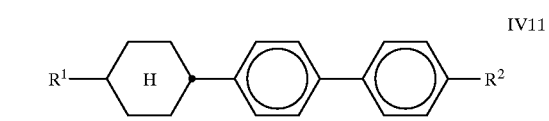

IV12
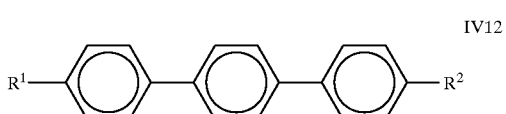

IV13
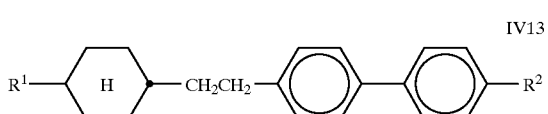

IV14
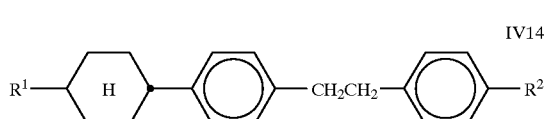

IV15
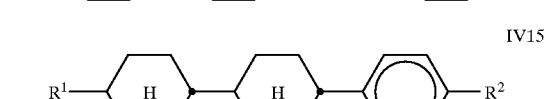

IV16
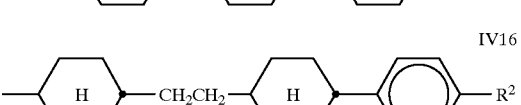

IV17
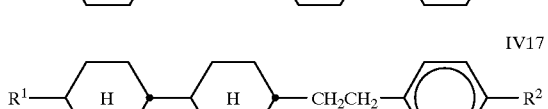

IV18
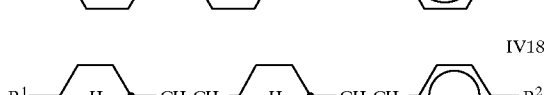

IV19
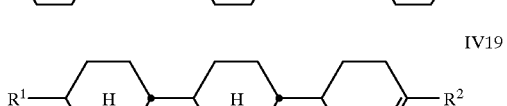

IV20
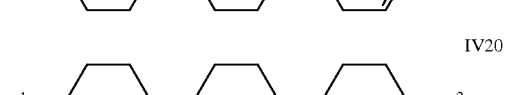

IV21
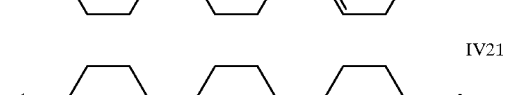

-continued

IV22
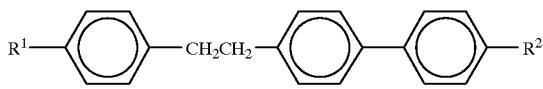

in which $R^1$ and $R^2$ are as defined for R, and the 1,4-phenylene groups in IV9 to IV18 may each, independently of one another, also be monosubstituted or polysubstituted by fluorine, where, in the compounds of the formula IV11 in which R' is an alkyl group having 1 to 12 carbon atoms in which at least one $CH_2$ group has been replaced by —CH=CH—, at least one of the 1,4-phenylene groups must be at least monosubstituted by fluorine.

Component B additionally comprises one or more compounds selected from the group consisting of the compounds of the formulae IV23 to IV28

IV23
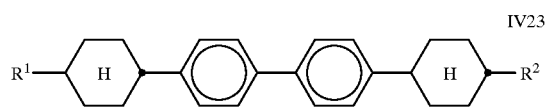

IV24
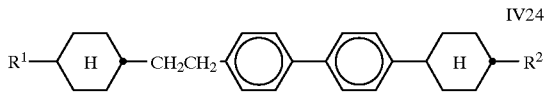

IV25
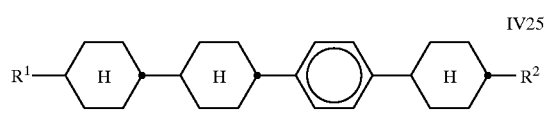

IV26
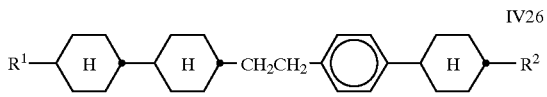

IV27
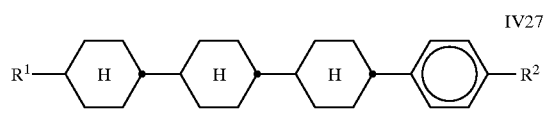

IV28
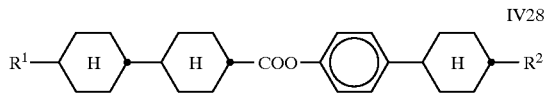

in which $R^1$ and $R^2$ are as defined for R, and the 1,4-phenylene groups in IV23 to IV28 may also each, independently of one another, be monosubstituted or polysubstituted by fluorine.

Component B comprises one or more compounds selected from the group consisting of IV29 and IV30:

IV29
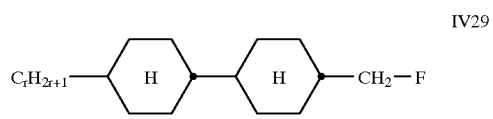

IV30
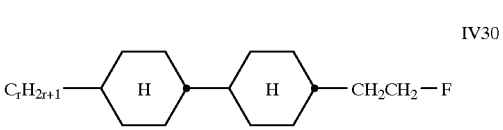

in which $C_xH_{2r+1}$ is a straight-chain alkyl group having up to 9 carbon atoms.

In addition to components A, B and C, the liquid-crystal mixture additionally comprises one or more compounds selected from the group consisting of the compounds of the formulae III and IV, in which $R^1$ and $R^2$ are as defined for R:

III
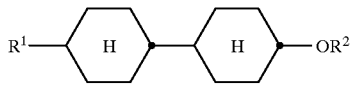

IV
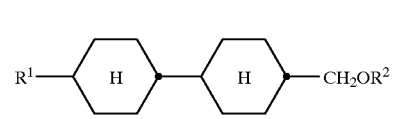

Preferred liquid-crystal mixtures comprise at least one component selected from the group consisting of the following compounds:

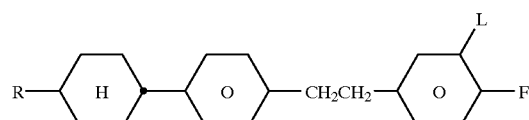

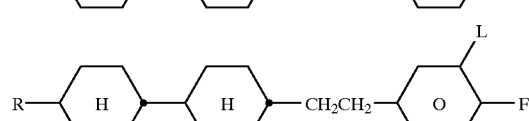

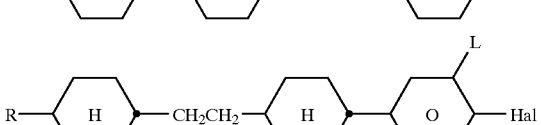

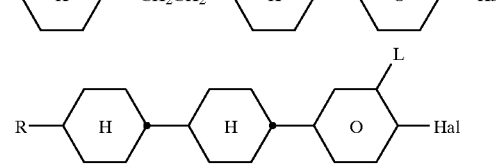

in which Hal is F or Cl, and L is H or F, and R is as defined above.

The liquid-crystal mixtures likewise comprise an optically active component C in such an amount that the ratio between the layer thickness (separation of the plane-parallel outer plates) and the natural pitch of the chiral nematic liquid-crystal mixture is greater than 0.2. For the component, a multiplicity of chiral dopes, some commercially available, is available to the person skilled in the art, for example such as cholesteryl nonanoate, S811 from Merck KGaA, Darmstadt, FRG, and CB 15 (BDH, Poole, UK). The choice of dopes is not crucial per se.

The novel liquid-crystal mixture preferably comprises one or more compounds selected from Group B1 consisting of compounds of the formulae B1I to B1IV:

B1I
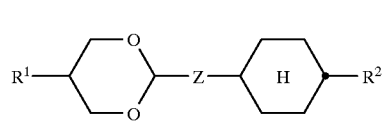

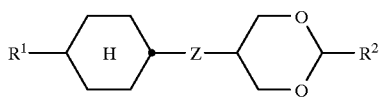

B1II

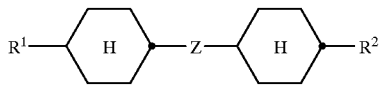

B1III

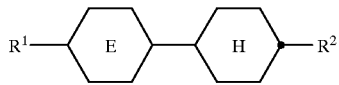

B1IV in which

R¹ and R² are each, independently of one another, as defined for R,

Z is —CH₂CH₂—, —CO—O—, —O—CO— or a single bond, and,

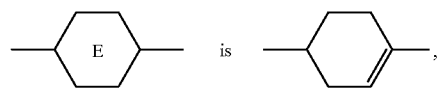

and/or at least one compound selected from Group B2 consisting of compounds of the formulae B1V to B1VII:

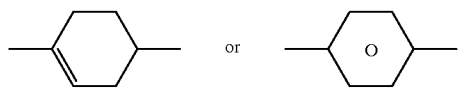

B1V

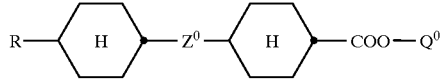

B1VI

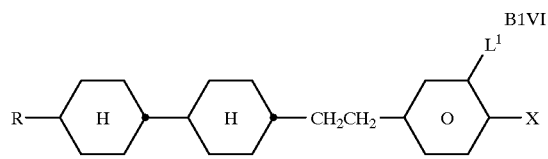

B1VII in which

R is as defined above,
Z° is —CH₂CH₂— or a single bond,
Q0 is

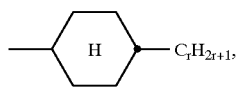 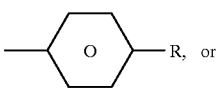

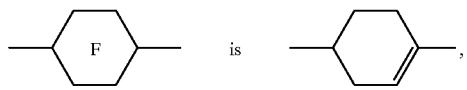

where r is 1–9,

X is CN or F,

L¹ is H or F, and/or at least one compound selected from Group B3 consisting of compounds of the formulae B1VIII, B1IX and B1X:

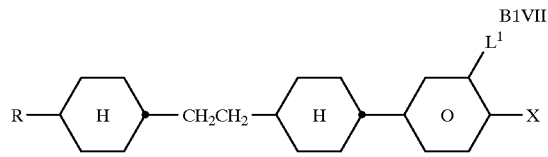

B1VIII

B1IX

B1X

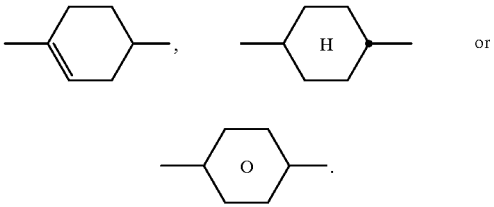

in which

R¹ and R², independently of one another, are as defined for R,

Y is F or Cl, and

In a particularly preferred embodiment, the novel mixtures comprise from about 5 to 35%, in particular from 5 to 20%, of liquid-crystalline tolan compounds. This enables smaller layer thicknesses (about 5–6 µm) to be used, significantly shortening the response times. Particular preference is given to mixtures comprising one or more compounds selected from Group T consisting of the compounds of the formulae T1 to T3:

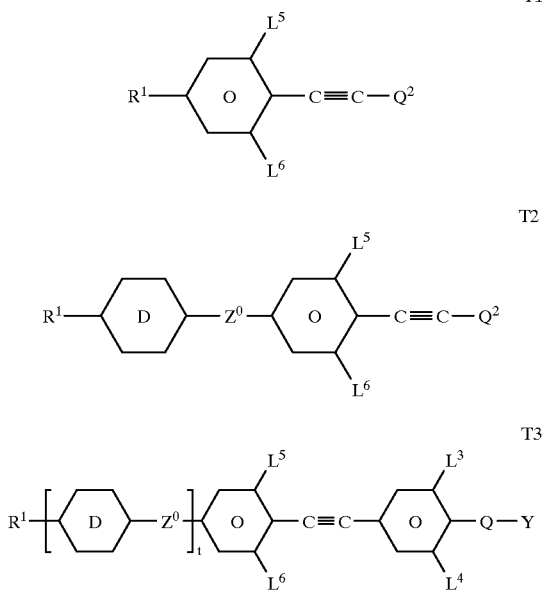

in which Q2 is

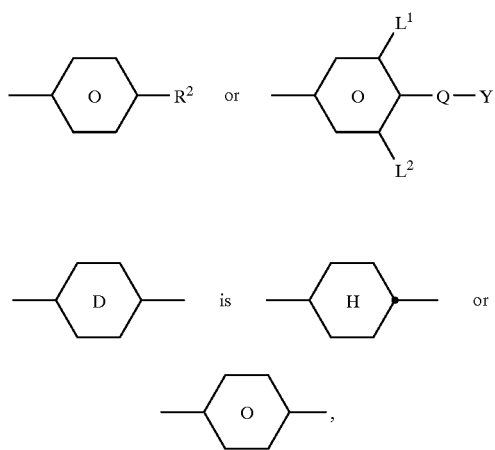

preferably

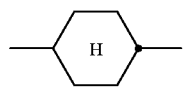

t is 0 or 1
$L^{1-6}$ are each, independently of one another, H or F
Q is —$CF_2$—, —CHF—, —$OCF_2$—, —OCHF— or a single bond
Y is F or Cl
$R^1$ and $R^2$ are each, independently of one another, as defined for R.

The proportion of compounds from the group T is preferably from 5 to 30%, in particular from 5 to 20%.

Component B preferably comprises one or more compounds of the formulae X to XII:

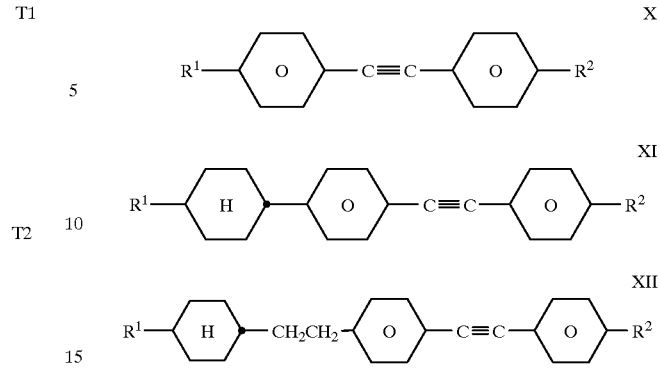

in which
$R^1$ and $R^2$ are each, independently of one another, as defined for R, and $R^1$ is preferably alkyl having 1 to 4 carbon atoms, in particular 1 to 2 carbon atoms, and $R^2$ is preferably alkoxy having 1 to 4 carbon atoms, in particular 1 to 2 carbon atoms.

The proportion of compounds from group B1 is preferably from 10 to 50%, in particular from 15 to 40%. Compounds of the formula B1III and B1IV are preferred.

Particularly preferred compounds of the formula B1III are those of the following subformulae B1IIIa and B1IIIb

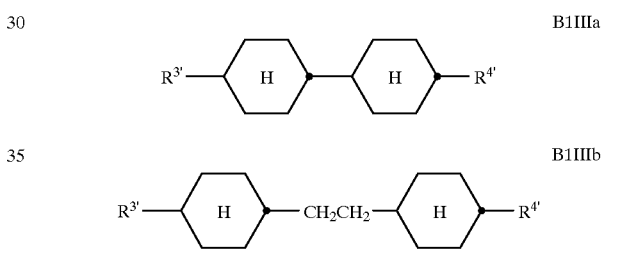

in which
$R^{3'}$ is $CH_3$—$(CH_2)_o$—O—, $CH_3$—$(CH_2)_p$—, trans-H—$(CH_2)_q$—CH=CH—$(CH_2CH_2)_b$—$CH_2$O— or trans-H—$(CH_2)_q$—CH=CH—$(CH_2CH_2)_b$—, $CH_3$—$(CH_2)_o$—O—$CH_2$—,
$R^{4'}$ is $CH_3$—$(CH_2)_p$—,
o is 1, 2, 3 or 4,
q is 0, 1, 2 or 3,
b is 0 or 1, and
p is 1, 2, 3 or 4.

Particular preference is given to compounds of the formula B1III in which one of the radicals $R^3$ or $R^4$ is O—$(CH_2)_o$—$CH_3$ or $CH_2$—O—$(CH_2)_o$—$CH_3$.

Preference is furthermore given to the compounds of the subformula

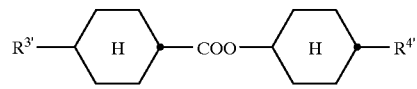

in which $R^{3'}$ and $R^{4'}$ are each, independently of one another, as defined above.

The proportion of compounds of the formula B1III of the abovementioned subformulae is preferably from about 5 to 45%, particularly preferably from about 10% to 35%. Particularly preferred compounds of the formula B1IV are those of the following subformula

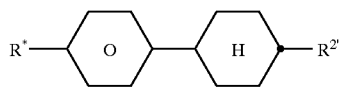

in which

R* is $CH_3-(CH_2)_o-O-$ or trans-$H-(CH_2)_q-CH=CH-(CH_2CH_2)_b-CH_2O-$, and $R^{2'}$ is $CH_3-(CH_2)_p-$, where o is 1, 2, 3 or 4, q is 0, 1, 2 or 3, b is 0 or 1, and p is 1, 2, 3 or 4.

The proportion of these compounds or of compounds of the formula BIV is preferably from about 5 to 40%, particularly preferably from about 10 to 35%.

The mixtures preferably comprise compounds of the formula B1III, in particular those of the subformula

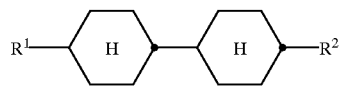

In a particularly preferred embodiment, the mixtures simultaneously comprise compounds of the formulae B1III and B1IV, where the total proportion of components from group B1 remains observed.

If compounds of the formulae B1I and B1III are present, $R^1$ and $R^2$ are preferably each, independently of one another, n-alkyl having 1 to 7 carbon atoms or (trans)-n-alkenyl having 3 to 7 carbon atoms. Z is preferably a single bond.

Preference is furthermore given to novel mixtures which comprise one or more compounds of the formula B1IV in which

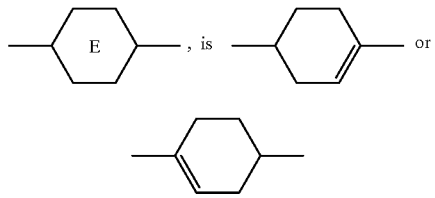

and $R^1$ and $R^2$ have one of the preferred meanings given above, particularly preferably n-alkyl having 1 to 7 carbon atoms.

In all cases, the total proportion of components from group B1 remains observed.

The proportion of compounds from group B2 is preferably from about 5 to 45%, in particular from 5 to 20%. The proportion (preferred ranges) for B1V to B1VII is as follows:

B1V: from about 5 to 30%, preferably from about 5 to 15%

Sum of B1VI and B1VII: from about 5 to 25%, preferably from about 10 to 20%.

Preferred compounds from group B2 are shown below:

B1V1

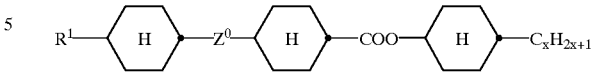

B1V2

B1V3

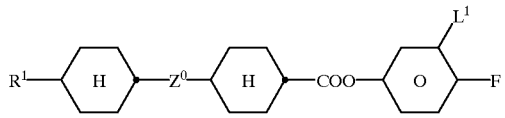

B1VI1

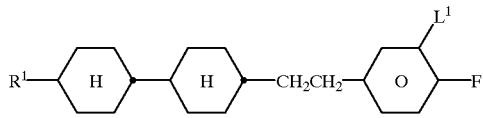

B1VII1

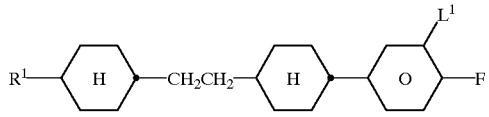

R is preferably n-alkyl having 1 to 7 carbon atoms or (trans)-n-alkenyl having 3 to 7 carbon atoms. $Z^0$ is preferably a single bond. $R^1$ preferably has the preferred meaning given above for R or is fluorine. $L^1$ is preferably fluorine. x is 1–15.

The novel mixtures preferably comprise one or more compounds selected from the group consisting of B1V3, B1VI1 and B1VII1 in a total proportion of from about 5 to 35%.

In a particularly preferred embodiment, the novel mixtures, in addition to B1V3, B1VI1 and B1VII1 (R=F), comprise further terminally fluorinated compounds selected, for example, from the group consisting of

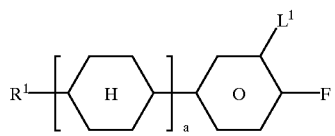

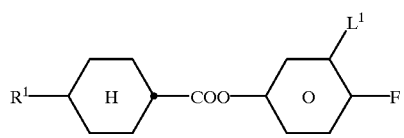

and/or polar heterocyclic compounds selected from the group consisting of

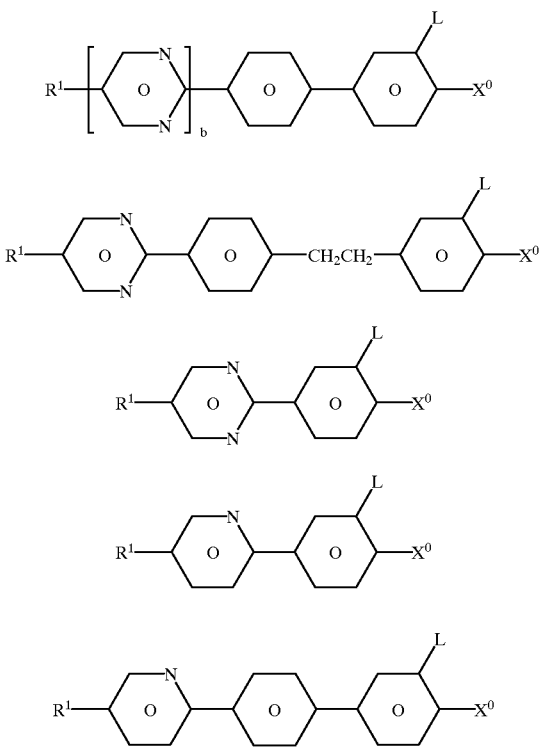

in which $R^1$ is preferably n-alkyl having 1 to 7 carbon atoms or (trans)-n-alkenyl having 3 to 7 carbon atoms, a is 1 or 2, b is 0 or 1, $X^o$ is F, Cl, $CF_3$, $—OCF_3$ or $—OCHF_2$, and L is H or F.

The total proportion of all terminally fluorinated compounds is preferably from about 5 to 65%, in particular from about 15 to 40%.

The proportion of compounds from group B3 is preferably from about 5 to 30%, particularly preferably from about 10 to 20%. $R^2$ is preferably n-alkyl or n-alkoxy, in each case having 1 to 9 carbon atoms.

However, it is also possible to use analogous compounds containing alkenyl or alkenyloxy groups. Compounds of the formula B1VIII are preferred.

The novel mixtures preferably comprise compounds of the formula I and compounds from at least one of groups B1, B2 and B3. They preferably comprise one or more compounds from group B1 and one or more compounds from group B2 and/or B3.

The proportion of compounds of component D is preferably from 0 to 20%, in particular from 0 to 10%.

In a particularly preferred embodiment, the novel mixtures preferably comprise from about 5 to 20% of one or more compounds having a dielectric anisotropy of below −2 (component D). Compounds of this type are known, for example derivatives of 2,3-dicyanohydro-quinones or cyclohexane derivatives containing the structural unit

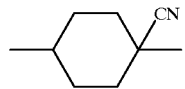

as described in DE-A 32 32 707 or DE-A 34 07 013.

However, preference is given to compounds containing the structural unit 2,3-difluoro-1,4-phenylene, for example compounds as described in DE-A 38 07 801, 38 07 861, 38 07 863, 38 07 864 or 38 07 908. Particular preference is given to tolans containing this structural unit, as described in International Patent Application PCT/DE 88/00133, in particular those of the formulae

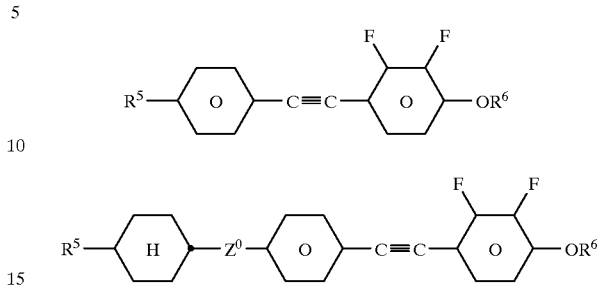

in which $R^5$ and $R^6$ are each, independently of one another, preferably n-alkyl having 1 to 7 carbon atoms or n-alkenyl having 3 to 7 carbon atoms, and $Z^0$ is $—CH_2CH_2—$ or a single bond.

Particular preference is given to phenyl cyclohexylcarboxylates of the formulae

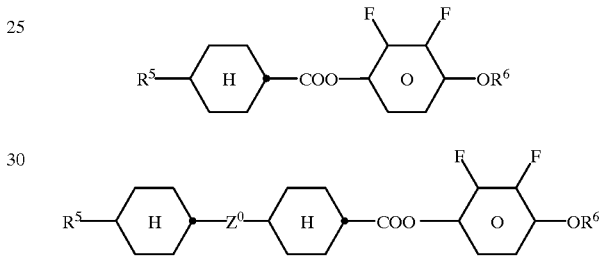

Component D comprises one or more compounds selected from the group consisting of V to IX:

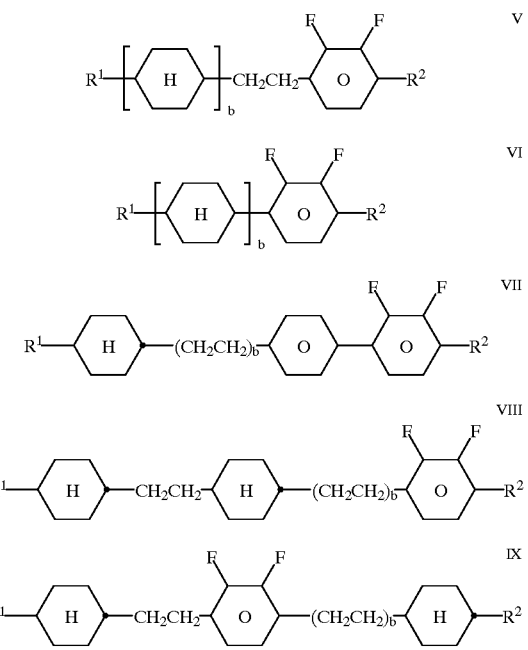

in which $R^1$ and $R^2$ are as defined for R, and b is 0 or 1.

Component B comprises one or more compounds selected from the group consisting of Xa to XIIa

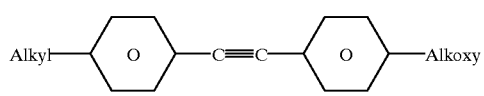
Xa

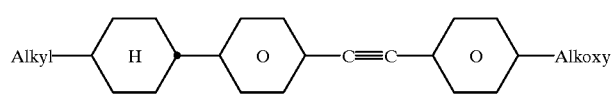
XIa

XIIa in which Alkyl and Alkoxy are an alkyl or alkoxy radical having 1 to 7 carbon atoms.

Component D in particular results in increased steepness of the characteristic line.

In a particularly preferred embodiment, the mixtures comprise from about 5 to 35%, particularly preferably from about 5 to 20%, of liquid-crystalline tolan compounds. This allows smaller layer thicknesses (about 5–6 μm) to be used, significantly shortening the response times. Particularly preferred tolans are shown below:

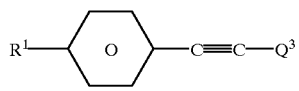
T1a

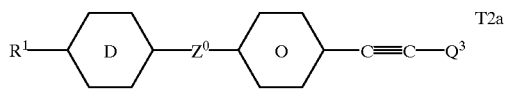
T2a $R^1$ is preferably n-alkyl or n-alkoxy having 1 to 7 carbon atoms, $Z^0$ is —CH$_2$CH$_2$— or a single bond,

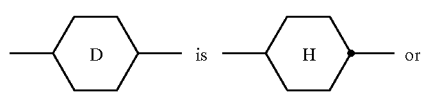

preferably

$Q^3$ is

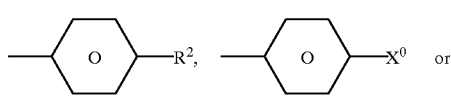 or

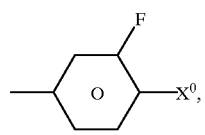

where $X^0$ is F, Cl or OCF$_3$, where $R^2$ is n-alkyl or n-alkoxy, in each case having 1 to 7 carbon atoms, or n-alkenyl or n-alkenyloxy, in each case having 3 to 7 carbon atoms.

Component A preferably comprises one or more compounds of the formula T3a

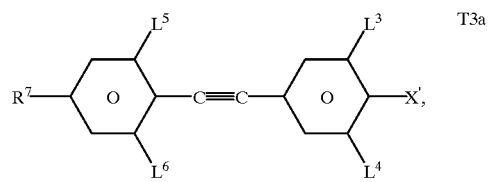
T3a in which $R^7$ is —C$_x$H$_{2x+1}$,

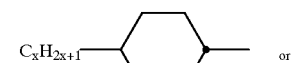 or

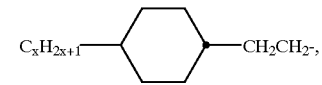

x is an integer from 1 to 15, $L^{3-6}$ are each, independently of one another, H or F, and X' is F, Cl or OCF$_3$.

Further particularly preferred embodiments are given below:

Component D comprises one or more compounds containing a 1-cyano-trans-1,4-cyclohexyl group or a 2,3-difluoro-1,4-phenylene group at least two compounds of the formulae AIII or AV compounds of the formulae AIII and AV at least one compound from the group consisting of:

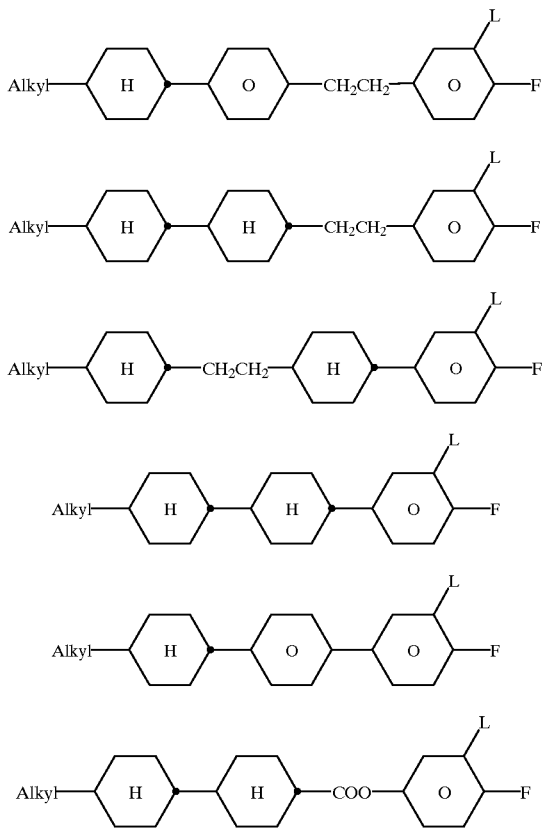

in which Alkyl is a straight-chain alkyl radical having 2 to 7 carbon atoms, and L is H or F;

one or more compounds in which R is a trans-alkenyl group or a trans-alkenyloxy group;

one or more compounds selected from the following group:

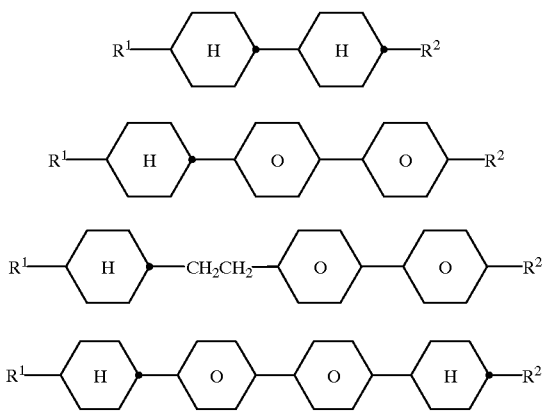

in which $R^1$ and $R^2$ have the preferred meanings given under compounds of component B. The 1,4-phenylene groups in the abovementioned compounds can also be substituted by fluorine. In the compounds

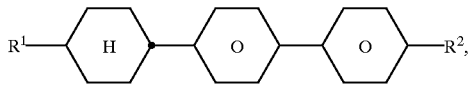

in which $R^1$ is an alkyl group having 1 to 12 carbon atoms in which at least one $CH_2$ group has been replaced by —CH=CH—, at least one of the 1,4-phenylene groups must be at least monosubstituted by fluorine. The proportion of these compounds in the liquid-crystal mixtures is from 0 to 25%, preferably from 5 to 15%.

In a further preferred embodiment, the mixtures comprise
one or more, in particular 1, 2, 3 or 4, compounds selected from the compounds of the formulae IIId, IIIb, IIIi and IIIp;
at least two compounds selected from the compounds of the formulae IIb1 or II'a;
one or more compounds of the formula B1IV;
one or more compounds of the formula T1 or T2;
one or more compounds of the formulae

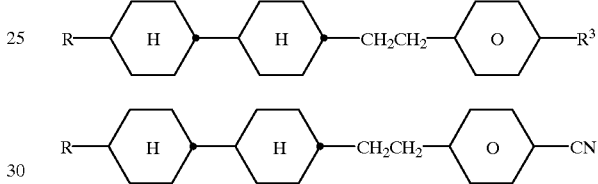

in which R is as defined under the formula III;
one or more compounds of the formulae

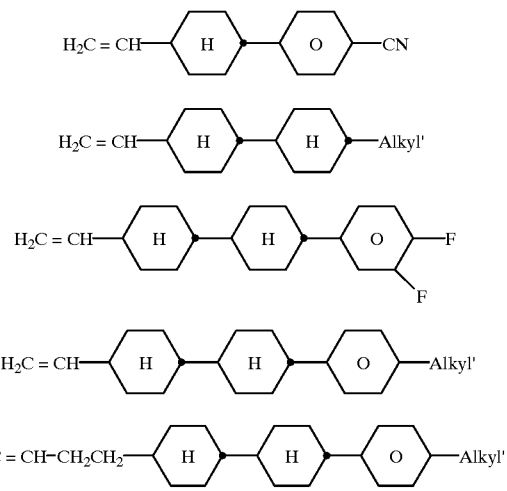

in which Alkyl' is an alkyl group having 1 to 12 carbon atoms.

In particular when used in SLCDs having high layer thicknesses, the novel mixtures are distinguished by very low overall response times ($=t_{on}+t_{off}$).

Low overall response times are an important criterion, in particular, in SLCDs for use as displays in laptops in order to be able to display cursor movements without interference.

The liquid-crystal mixtures used in the SLCDs according to the invention are dielectrically positive with $\Delta\epsilon \geq 1$. Particular preference is given to liquid-crystal mixtures where $\Delta\epsilon \geq 3$ and very particularly to those where $\Delta\epsilon \geq 5$.

The liquid-crystal mixtures according to the invention have favorable values for the threshold voltage $V_{10/0/20}$ and for the flow viscosity η. If the value for the optical path difference d.Δn is specified, the value for the layer thickness d is determined by the optical anisotropy Δn. In particular at relatively high values for d.Δn, the use of liquid-crystal mixtures according to the invention having a relatively high value for the optical anisotropy is generally preferred since the value for d can then be chosen to be relatively small, which results in more favorable values for the response times. However, liquid-crystal displays according to the invention which contain liquid-crystal mixtures according to the invention having relatively small values for Δn are also characterized by advantageous values for the response times. The liquid-crystal mixtures according to the invention are furthermore characterized by advantageous values for the steepness of the electrooptical characteristic line and can be operated at high multiplex rates. In addition, the liquid-crystal mixtures according to the invention have high stability and favorable values for the electrical resistance and the frequency dependence of the threshold voltage. The liquid-crystal displays according to the invention have a broad operating temperature range and good angle dependence of the contrast.

The construction of the liquid-crystal display elements according to the invention from polarizers, electrode baseplates and electrodes with a surface treatment such that the preferential alignment (director) of the liquid-crystal molecules in each case adjacent thereto is usually twisted by a value of from 160° to 720° from one electrode to the next, corresponds to the structure which is conventional for display elements of this type. The term conventional structure here is broadly drawn and also includes all derivatives and modifications of the supertwist cell, in particular also matrix display elements, and display elements which contain additional magnets. The surface tilt angle at the two outer plates may be identical or different. Identical tilt angles are preferred.

An essential difference of the display elements according to the invention to those customary hitherto based on the twisted nematic cell is, however, the choice of the liquid-crystal components of the liquid-crystal layer.

The liquid-crystal mixtures which can be used according to the invention are prepared in a manner which is known per se. In general, the desired amount of the components used in a lesser amount is dissolved in the components making up the principal constituent, expediently at elevated temperature. It is also possible to mix solutions of the components in an organic solvent, for example in acetone, chloroform or methanol, and, after mixing, to remove the solvent again, for example by distillation.

The dielectrics may also contain further additives which are known to a person skilled in the art and are described in the literature. For example, 0–15% of pleochroic dyes may be added.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents, and publications, cited above and below, and of corresponding German application 196 49 678.0 filed Nov. 30, 1996, are hereby incorporated by reference.

EXAMPLES

The examples below are intended to illustrate the invention without representing a limitation.

The following abbreviations are used:

| | |
|---|---|
| S-N | smectic-nematic phase transition temperature, |
| N-I | nematic-isotropic phase transition temperature, |
| c.p. | clearing point, |
| visc. | viscosity (mPa · s), |
| $t_{on}$ | time from switching on until 90% of the maximum contrast is achieved, |
| $t_{off}$ | time from switching off until 10% of the maximum contrast is achieved. |
| Steepness | $[(V_{90}/V_{10}) - 1] \cdot 100\%$ |
| $t_{ave}$ | $\frac{t_{on} + t_{off}}{2}$ (average response time). |

The SLCD is operated in multiplex mode (multiplex ratio 1:240, bias 1:16)

Above and below, all temperatures are indicated in °C. The percentages are per cent by weight. The values for the response times and viscosities relate to 20° C.

In the present application and in the examples below, the structures of the liquid-crystal compounds are indicated by acronyms, the transformation into chemical formulae taking place in accordance with tables A and B below. All radicals $C_nH_{2n+1}$ and $C_mH_{2m+1}$ are straight-chain alkyl radicals having n and m carbon atoms respectively. The coding in Table B is self-evident. In Table A, only the acronym for the parent structure is given. In individual cases, the acronym for the parent structure is followed, separated by a dash, by a code for the substituents $R^1$, $R^2$, $L^1$ and $L^2$:

| Code for $R^1$, $R^2$, $L^1$, $L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | H | F |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | H | F |
| nmF | $C_nH_{2n+1}$ | $C_mH_{2m+1}$ | F | H |
| $nCF_3$ | $C_nH_{2n+1}$ | $CF_3$ | H | H |
| $nOCF_3$ | $C_nH_{2n+1}$ | $OCF_3$ | H | H |
| $nOCF_2$ | $C_nH_{2n+1}$ | $OCHF_2$ | H | H |
| nS | $C_nH_{2n+1}$ | NCS | H | H |
| rVsN | $C_rH_{2r+1}$—CH=CH—$C_sH_{2s}$— | CN | H | H |
| rEsN | $C_rH_{2r+1}$—O—$C_sH_{2s}$— | CN | H | H |
| nAm | $C_nH_{2n+1}$ | $COOC_mH_{2m+1}$ | H | H |
| nF.Cl | $C_nH_{2n+1}$ | Cl | H | F |

TABLE A
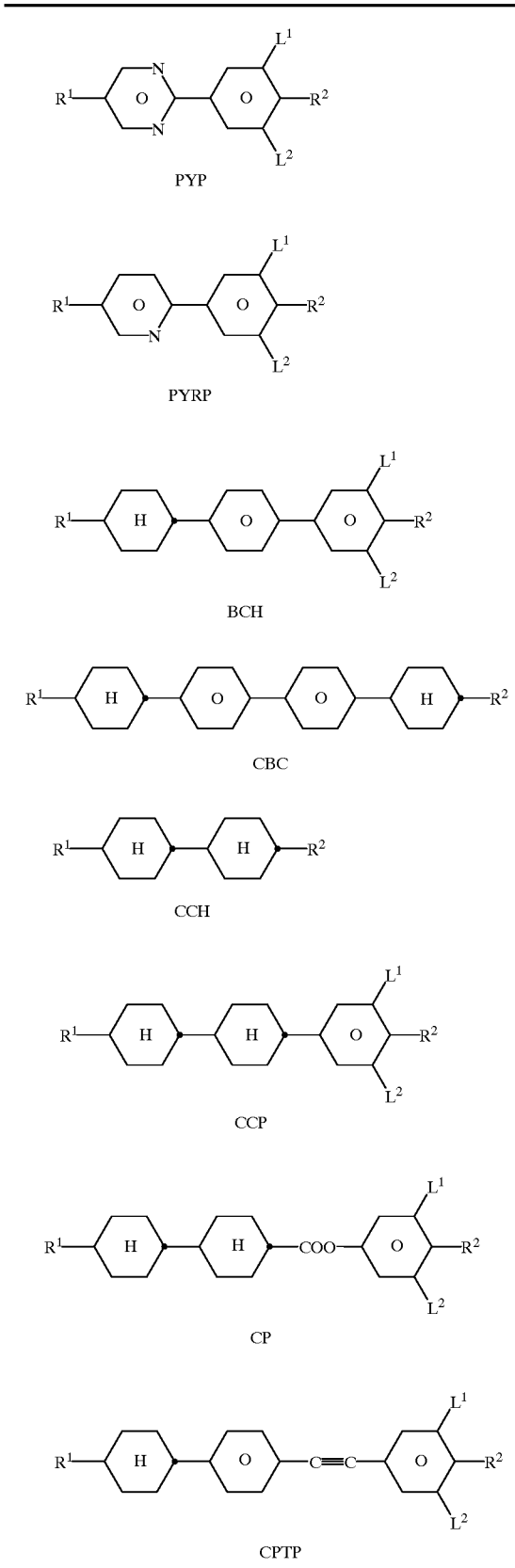
PYP
PYRP
BCH
CBC
CCH
CCP
CP
CPTP
TABLE A-continued
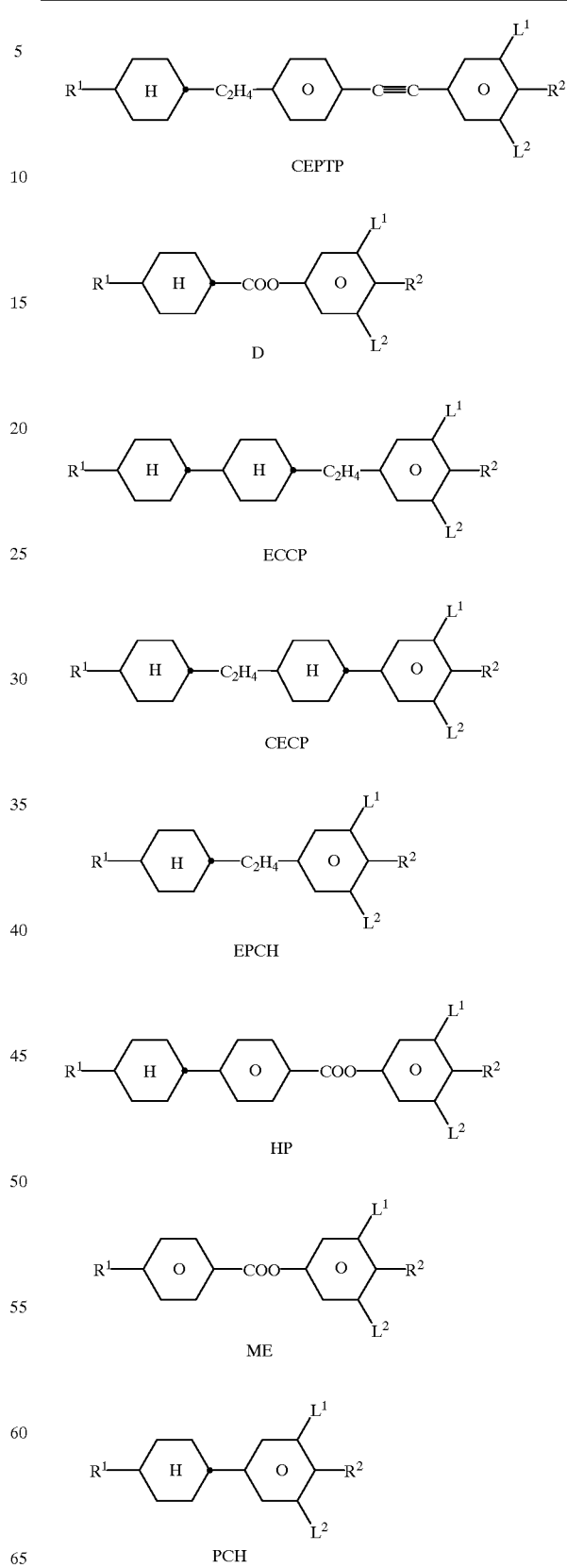
CEPTP
D
ECCP
CECP
EPCH
HP
ME
PCH TABLE A-continued
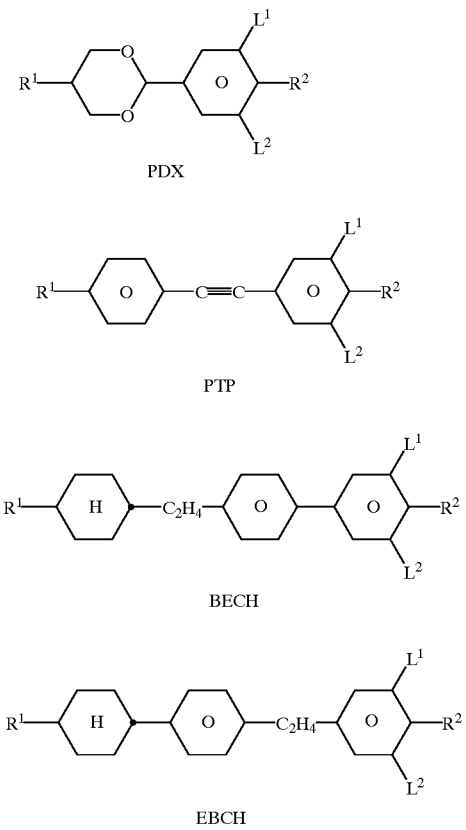
PDX
PTP
BECH
EBCH
TABLE A-continued
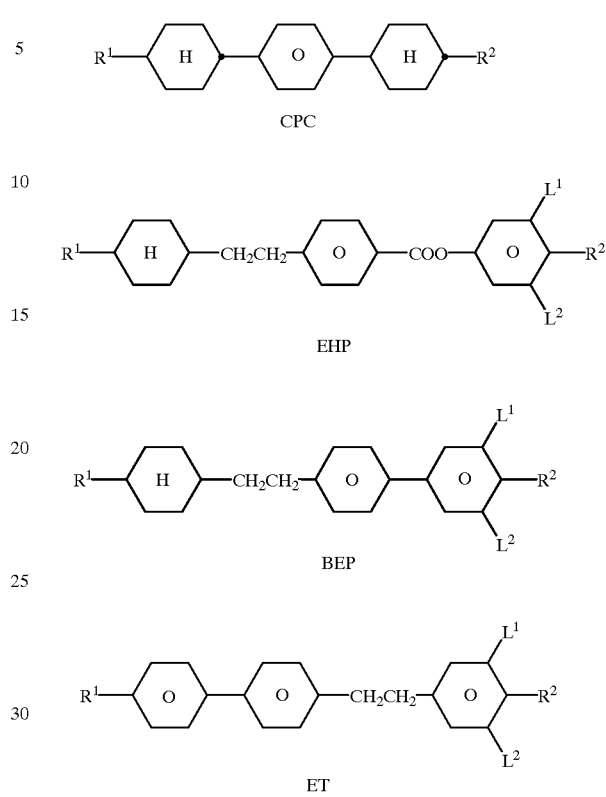
CPC
EHP
BEP
ET
TABLE B
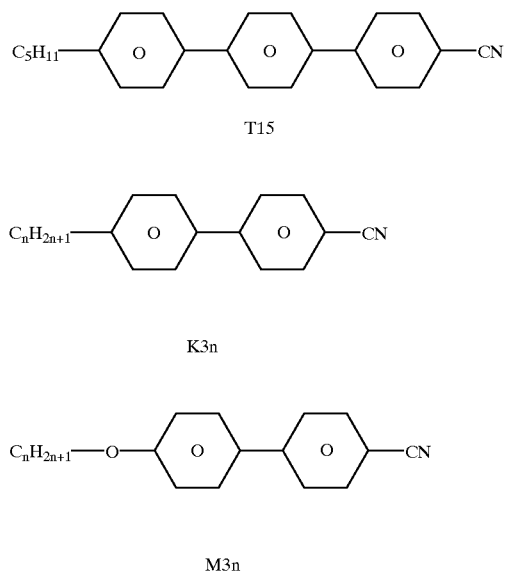
T15
K3n
M3n TABLE B-continued
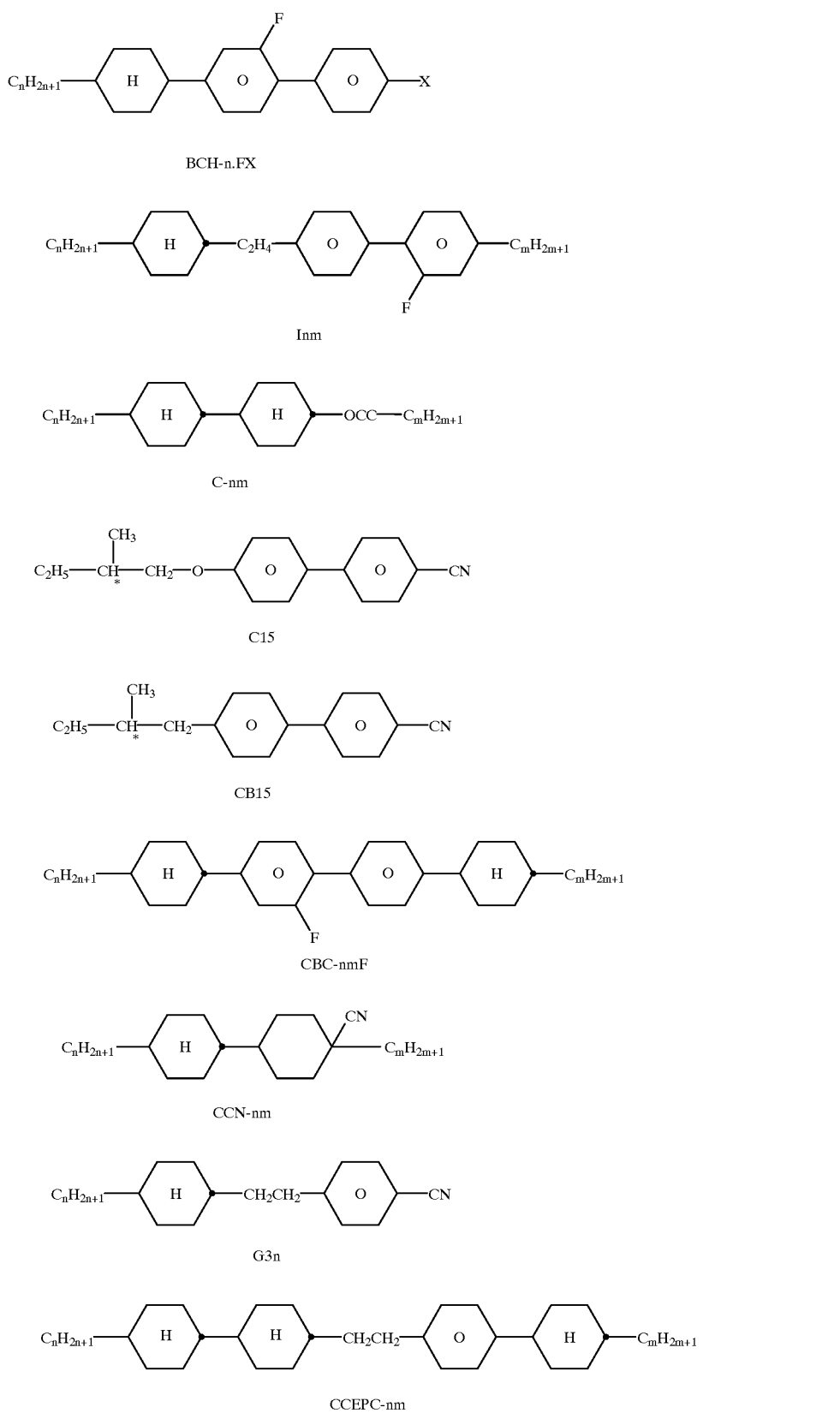

TABLE B-continued
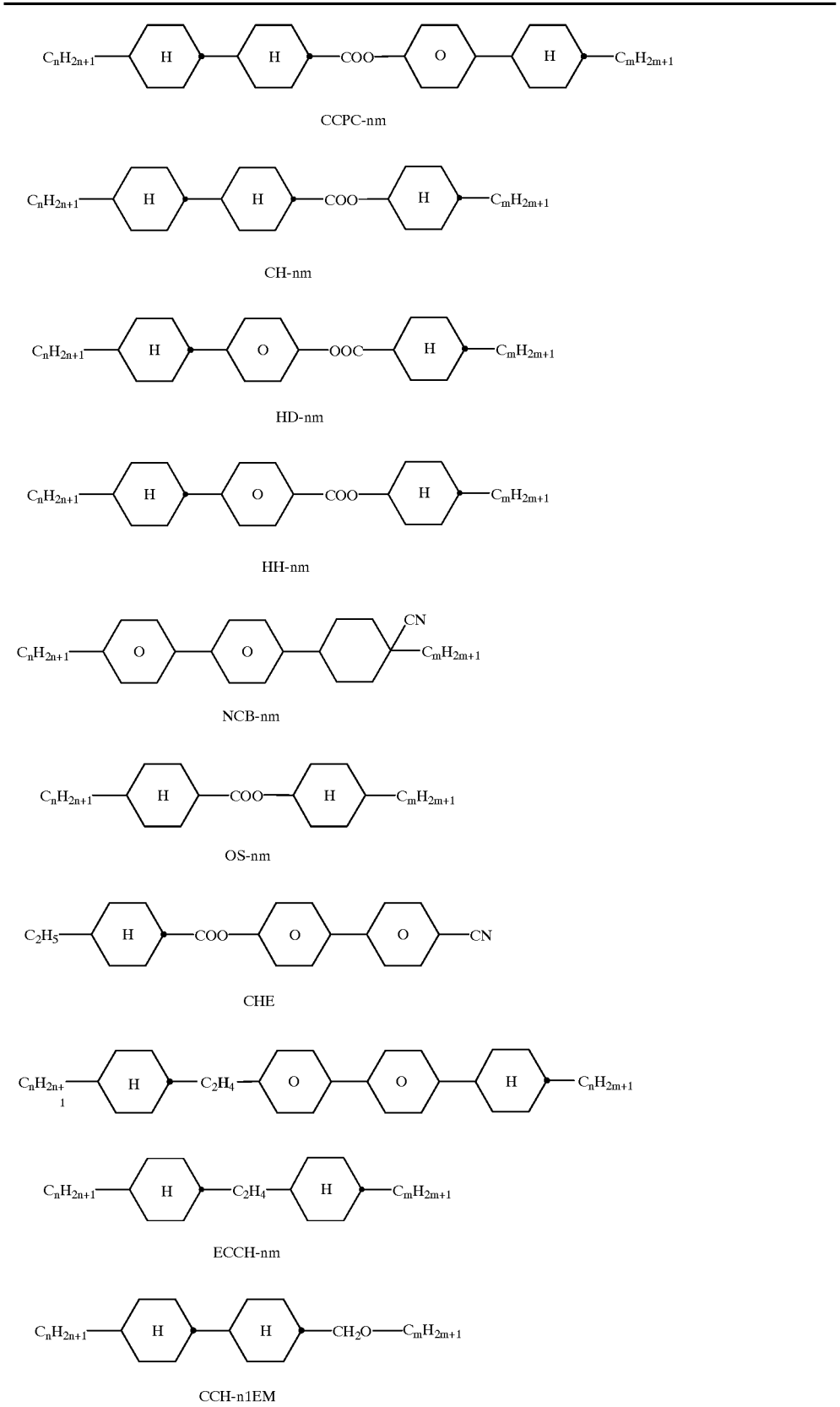

TABLE B-continued
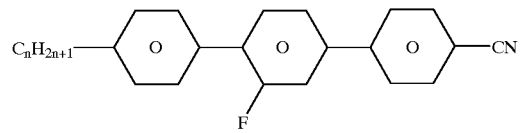
T-nFN
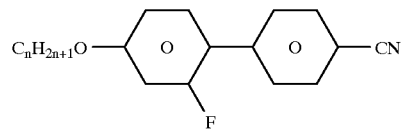
B-nO.FN
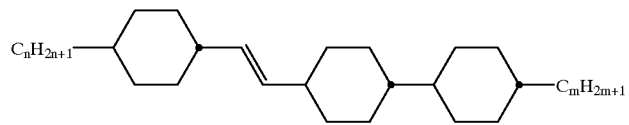
CVCC-n-m
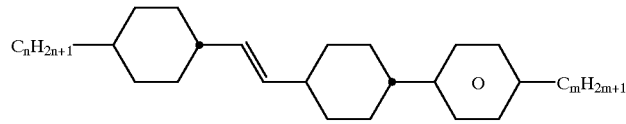
CVCP-n-m
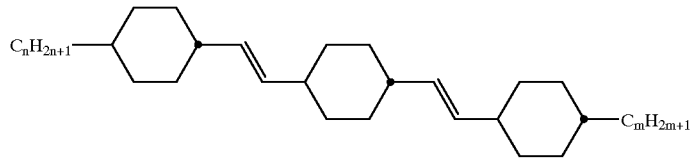
CVCVC-n-m
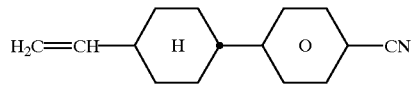
CP-V-N
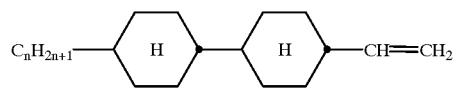
CC-n-V
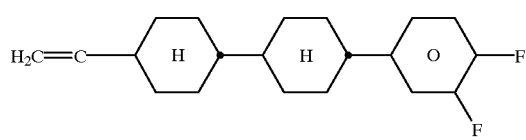
CCG-V-F TABLE B-continued

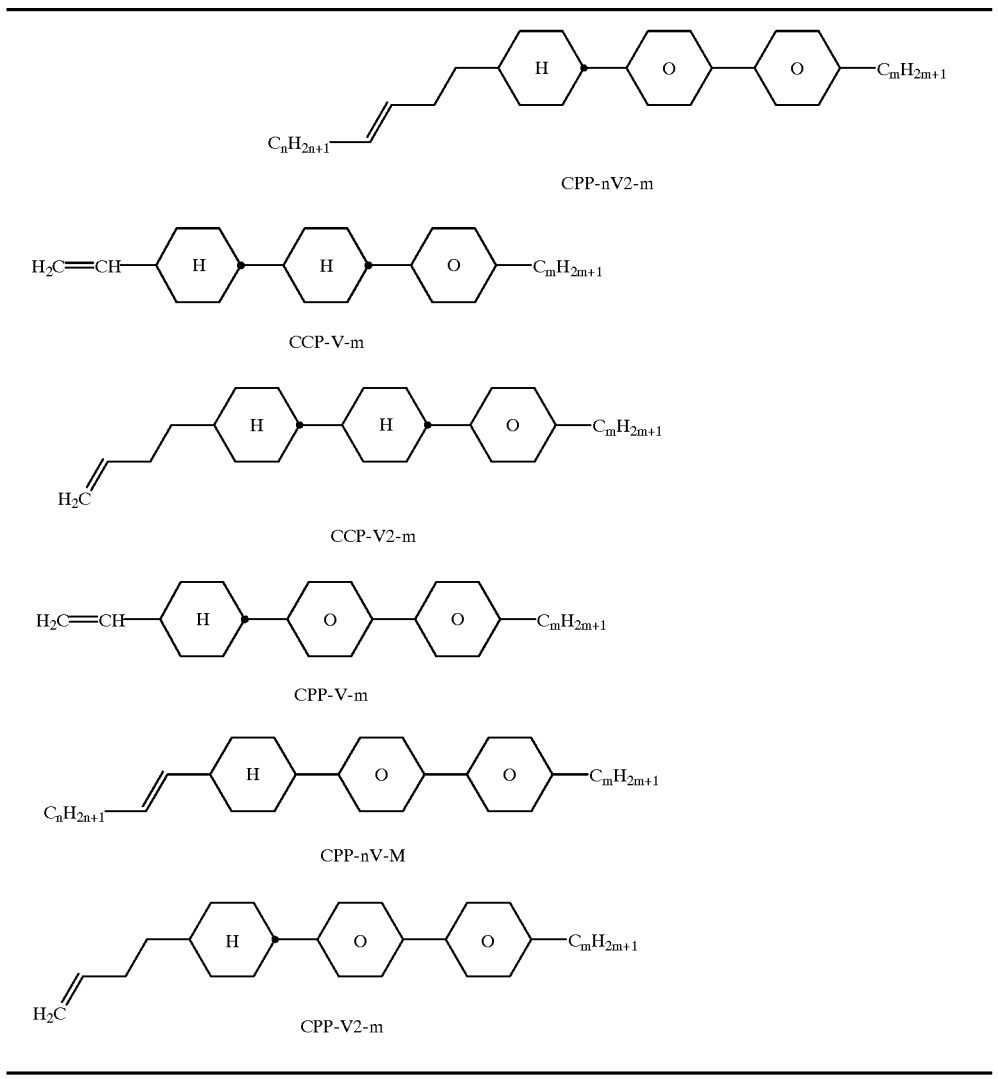

The examples below are intended to illustrate the invention without representing a limitation. Above and below, percentages are per cent by weight. All temperatures are given in degrees celcius. Δn denotes optical anisotropy (589 nm, 20° C.), and the viscosity (mm$^2$/sec) was determined at 20° C.

MIXTURE EXAMPLES

Example A

| | | | |
|---|---|---|---|
| CP-V-N | 9.8% | Clearing point [° C.]: | +109 |
| ME2N.F | 3.0% | Δn [589 nm; 20° C.]: | +0.126 |
| ME3N.F | 2.3% | STN 240° | |
| ME4N.F | 5.5% | d.Δn [μm]: | 0.85 |
| CC-5-V | 20.7% | $V_{(10,0,20)}$ [V]: | 2.57 |
| CCG-V-F | 5.8% | Steepness [%]: | 5.3 |
| CPP-1V2-2 | 12.4% | $t_{ave}$ [ms]: | 253 |
| CPTP-302 | 8.6% | d/p: | 0.53 |
| CCP-V-1 | 16.0% | | |
| CCP-V2-1 | 15.9% | | |

Example B

| | | | |
|---|---|---|---|
| CP-V-N | 9.8% | Clearing point [° C.]: | +107 |
| ME2N.F | 3.0% | Δn [589 nm; 20° C.]: | +0.126 |
| ME3N.F | 2.3% | STN 240° | |
| ME4N.F | 5.5% | d.Δn [μm]: | 0.85 |
| CC-5-V | 20.7% | $V_{(10,0,20)}$ [V]: | 2.50 |
| CCG-V-F | 5.8% | Steepness [%]: | 5.7 |
| CPP-V-2 | 8.0% | $t_{ave}$ [ms]: | 243 |
| CPP-1V2-2 | 4.4% | d/p: | 0.53 |
| CPTP-302 | 8.6% | | |
| CCP-V-1 | 16.0% | | |
| CCP-V2-1 | 15.9% | | |

Example C

| | | | |
|---|---|---|---|
| PCH-2 | 9.8% | Clearing point [° C.]: | +108 |
| ME2N.F | 3.0% | Δn [589 nm; 20° C.]: | +0.1271 |
| ME3N.F | 2.3% | STN 240° | |
| ME4N.F | 5.5% | d.Δn [μm]: | 0.85 |
| CC-5-V | 20.7% | $V_{(10,0,20)}$ [V]: | 2.45 |
| CCG-V-F | 5.8% | Steepness [%]: | 5.8 |

-continued

| | | | |
|---|---|---|---|
| CPP-V-2 | 6.0% | $t_{ave}$ [ms]: | 238 |
| CPP-V-1 | 6.0% | d/p: | 0.53 |
| CPTP-302 | 9.0% | | |
| CCP-V-1 | 16.0% | | |
| CCP-V2-1 | 15.9% | | |

Example D

| | | | |
|---|---|---|---|
| CP-V-N | 9.8% | Clearing point [° C.]: | +108 |
| ME2N.F | 3.0% | Δn [589 nm; 20° C.]: | +0.1277 |
| ME3N.F | 2.3% | SN 240° | |
| ME4N.F | 5.5% | d.Δn [μm]: | 0.85 |
| CC-5-V | 20.7% | $V_{(10,0,20)}$ [V]: | 2.38 |
| CCG-V-F | 5.8% | Steepness [%]: | 5.9 |
| CPP-V-1 | 12.4% | $t_{ave}$ [ms]: | 238 |
| CPTP-302 | 8.6% | d/p: | 0.53 |
| CCP-V-1 | 16.0% | | |
| CCP-V2-1 | 15.9% | | |

Example E

| | | | |
|---|---|---|---|
| CP-V-N | 9.8% | Clearing point [° C.]: | +105 |
| ME2N.F | 3.0% | Δn [589 nm; 20° C.]: | +0.126 |
| ME3N.F | 2.3% | STN 240° | |
| ME4N.F | 5.5% | d.Δn [μm]: | 0.85 |
| CC-5-V | 20.7% | $V_{(10,0,20)}$ [V]: | 2.46 |
| CCG-V-F | 5.8% | Steepness [%]: | 6.2 |
| CPP-V-2 | 12.4% | $t_{ave}$ [ms]: | 226 |
| CPTP-302 | 8.6% | d/p: | 0.53 |
| CCP-V-1 | 16.0% | | |
| CCP-V2-1 | 15.9% | | |

Example F

| | | | |
|---|---|---|---|
| CP-V-N | 9.8% | Clearing point [° C.]: | +110 |
| ME2N.F | 3.0% | Δn [589 nm; 20° C.]: | +0.1280 |
| ME3N.F | 2.3% | STN 240° | |
| ME4N.F | 5.5% | d.Δn [μm]: | 0.85 |
| CC-5-V | 20.7% | $V_{(10,0,20)}$ [V]: | 2.51 |
| CCG-V-F | 5.8% | Steepness [%]: | 5.6 |
| CPP-1V-2 | 12.4% | $t_{ave}$ [ms]: | 234 |
| CPTP-302 | 8.6% | d/p: | 0.53 |
| CCP-V-1 | 16.0% | | |
| CCP-V2-1 | 15.9% | | |

Example G

| | | | |
|---|---|---|---|
| CP-V-N | 9.8% | Clearing point [° C.]: | +107 |
| ME2N.F | 3.0% | Δn [589 nm; 20° C.]: | +0.1254 |
| ME3N.F | 2.3% | STN 240° | |
| ME4N.F | 5.5% | d.Δn [μm]: | 0.85 |
| CC-5-V | 20.7% | $V_{(10,0,20)}$ [V]: | 2.49 |
| CCG-V-F | 5.8% | Steepness [%]: | 6.2 |
| CPP-V2-2 | 12.4% | $t_{ave}$ [ms]: | 240 |
| CPTP-302 | 8.6% | d/p: | 0.53 |
| CCP-V-1 | 16.0% | | |
| CCP-V2-1 | 15.9% | | |

COMPARATIVE EXAMPLES

Example H

| | | | |
|---|---|---|---|
| PCH-2 | 9.8% | Clearing point [° C.]: | +109 |
| ME2N.F | 3.0% | Δn [589 nm; 20° C.]: | +0.1252 |
| ME3N.F | 2.3% | STN 240° | |
| ME4N.F | 5.5% | d.Δn [μm]: | 0.85 |
| CC-5-V | 20.7% | $V_{(10,0,20)}$ [V]: | 2.49 |
| CCG-V-F | 5.8% | Steepness [%]: | 6.0 |
| BCH-32 | 6.5% | $t_{ave}$ [ms]: | 258 |
| BCH-52 | 5.5% | d/p: | 0.53 |
| CPTP-302 | 9.0% | | |
| CCP-V-1 | 16.0% | | |
| CCP-V2-1 | 15.9% | | |

Example I

| | | | |
|---|---|---|---|
| PCH-3 | 7.0% | Clearing point [° C.]: | +109 |
| ME2N.F | 3.0% | Δn [589 nm; 20° C.) : | +0.1247 |
| ME3N.F | 2.3% | STN 240° | |
| ME4N.F | 5.5% | d.Δn [μm]: | 0.85 |
| CC-5-V | 20.3% | $V_{(10,0,20)}$ [V]: | 2.56 |
| CCG-V-F | 10.0% | Steepness [%]: | 6.4 |
| BCH-32 | 6.5% | $t_{ave}$ [ms]: | 235 |
| BCH-52 | 5.5% | d/p: | 0.53 |
| PTP-102 | 3.2% | | |
| CPTP-302 | 4.8% | | |
| CCP-V-1 | 16.0% | | |
| CCP-V2-1 | 15.9% | | |

Example J

| | | | |
|---|---|---|---|
| PCH-3 | 11.0% | Clearing point [° C.]: | +109 |
| ME2N.F | 3.0% | Δn [589 nm; 20° C.]: | +0.1245 |
| ME3N.F | 2.3% | STN 240° | |
| ME4N.F | 2.5% | d.Δn [μm]: | 0.85 |
| CC-5-V | 19.3% | $V_{(10,0,20)}$ [V]: | 2.70 |
| CCG-V-F | 10.0% | Steepness [%]: | 5.5 |
| BCH-32 | 6.5% | $t_{ave}$ [ms]: | 249 |
| BCH-52 | 5.5% | d/p: | 0.53 |
| PTP-102 | 3.2% | | |
| CPTP-302 | 4.8% | | |
| CCP-V-1 | 16.0% | | |
| CCP-V2-1 | 15.9% | | |

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A supertwist liquid-crystal display containing
   two plane-parallel outer plates which, together with a frame, form a cell,
   a nematic liquid-crystal mixture of positive dielectric anisotropy which is present in the cell,
   electrode layers with superposed alignment layers on the insides of the outer plates,
   a pitch angle between the longitudinal axis of the molecules at the surface of the outer plates and the outer plates of from about 1 degree to 30 degrees, and
   a twist angle of the liquid-crystal mixture in the cell from alignment layer to alignment layer with a value of between 100 and 600°, a nematic liquid crystal mixture comprising
- a) 10–65% by weight of a liquid-crystalline component A consisting of one or more compounds having a dielectric anisotropy of greater than +1.5;
- b) 20–90% by weight of a liquid-crystalline component B consisting of one or more compounds having a dielectric anisotropy of between −1.5 and +1.5;
- c) 0–20% by weight of a liquid-crystalline component D consisting of one or more compounds having a dielectric anisotropy of below −1.5, and
- d) an optically active component C in such an amount that the ratio between the layer thickness of the separation of the plane-parallel outer plates and the natural pitch of the chiral nematic liquid-crystal mixture is from about 0.2 to 1.3, wherein
component B comprises at least one compound of the formula I

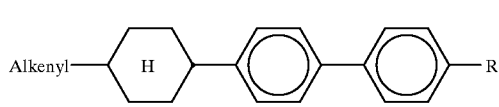

and component A comprises at least one compound of the formula I'

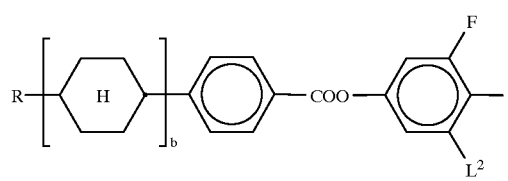

in which alkenyl is an alkenyl radical having 2 to 7 carbon atoms,

R is an alkyl group having 1 to 12 carbon atoms, in which, in addition, one or two non-adjacent $CH_2$ groups are optionally replaced by —O—, —CH=CH—, —CO—, —OCO— or —COO—, b is 0 or 1, and $L^2$ is H or F.

2. A display according to claim 1, wherein component A further comprises a compound of the formulae II, II' or III

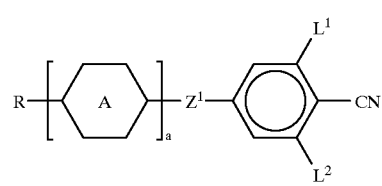

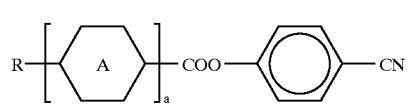

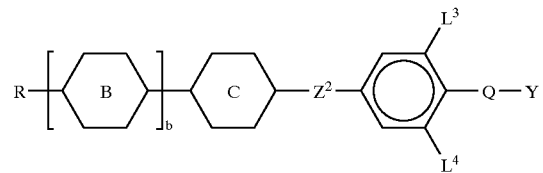

in which

R is an alkyl group having 1 to 12 carbon atoms, in which, in addition, one or two non-adjacent $CH_2$ groups are optionally replaced by —O—, —CH=CH—, —CO—, —OCO— or —COO—,

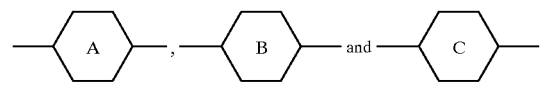

are each, independently of one another,

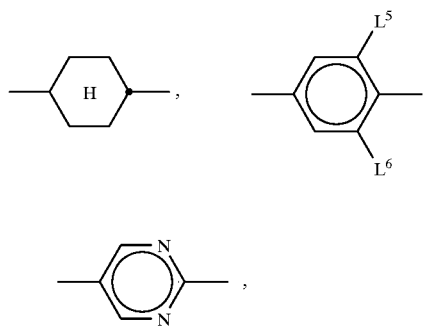

$L^{1-6}$ are each, independently of one another, H or F, $Z^1$ is —$CH_2CH_2$— or a single bond, $Z^2$ is —$CH_2CH_2$—, —COO—, —C≡C— or a single bond, Q is —$CF_2$—, —CHF—, —$OCF_2$—, —OCFH— or a single bond, Y is F or Cl, a is 1 or 2, and b is 0 or 1.

3. A display according to claim 1, wherein component A further comprises at least one compound selected from the formulae IIa to IIc and II'a

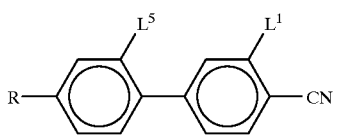

-continued

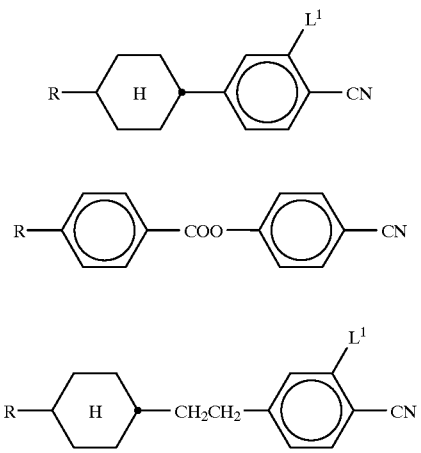

in which

R is an alkyl group having 1 to 12 carbon atoms, in which, in addition, one or two non-adjacent $CH_2$ groups are optionally replaced by —O—, —CH=CH—, —CO—, —OCO— or —COO—, and $L^1$ and $L^5$ are independently H or F.

4. A display according to claim 1, wherein component B further comprises one or more compounds of the following formulae

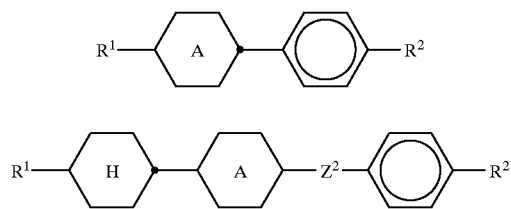

in which $R^1$ and $R^2$ are each, independently of one another, alkyl, alkoxy, alkenyl or alkenyloxy having 1–12 carbon atoms,

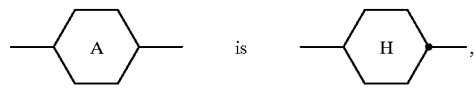

-continued

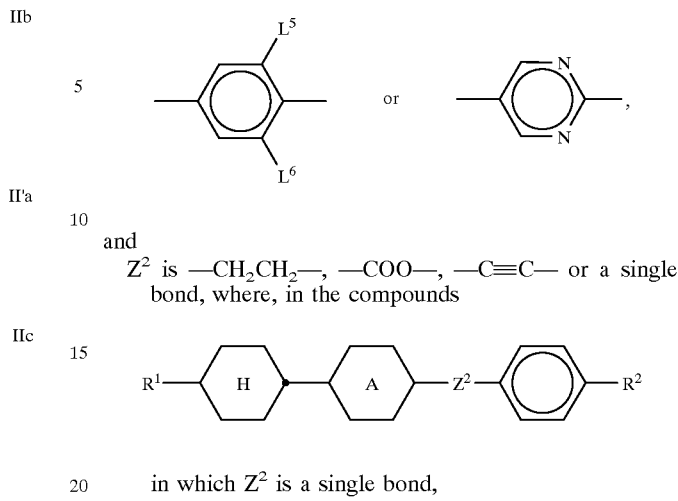

and $Z^2$ is —$CH_2CH_2$—, —COO—, —C≡C— or a single bond, where, in the compounds

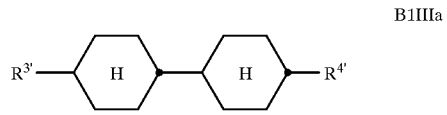

in which $Z^2$ is a single bond,

is 1,4-phenylene and $R^1$ is an alkenyl group having 1 to 12 carbon atoms, at least one of the 1,4-phenylene groups must be at least monosubstituted by fluorine.

5. A display according to claim 1, wherein the liquid crystal mixture further comprises one or more compounds of formula B1IIIa B1IIIa

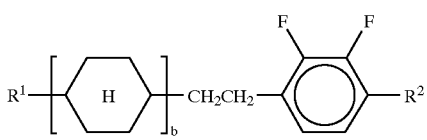

in which $R^{3'}$ is $CH_3$—$(CH_2)_o$—O—, $CH_3$—$(CH_2)_p$—, trans-H—$(CH_2)_q$CH=C—$(CH_2CH_2)_b$—$CH_2O$—, trans-H—$(CH_2)_q$—CH=CH—$(CH_2CH_2)_b$—, or $CH_3$—$(CH_2)_o$—O—$CH_2$—, $R^{4'}$ is $CH_3$—$(CH_2)_p$—, o is 1, 2, 3 or 4, q is 0, 1, 2 or 3, b is 0 or 1, and p is 1, 2, 3 or 4.

6. A display according to claim 1, wherein component D comprises one or more compounds selected from the group consisting of those of the formulae V to IX

V

-continued

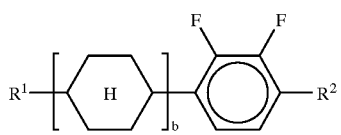

VI

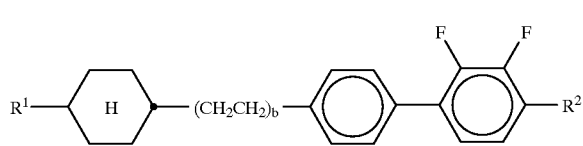

VII

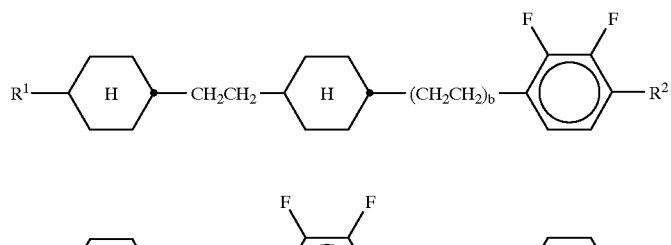

VIII

IX in which $R^1$ and $R^2$ are as defined for R and b is 0 or 1.

7. A display according to claim 1, wherein component B further comprises one or more compounds selected from the group consisting of those of the formulae Xa to XIIa

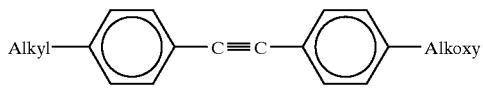

Xa

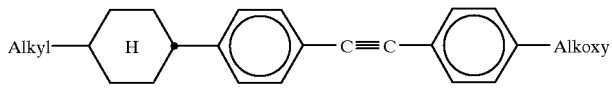

XIa

XIIa in which the alkyl and alkoxy radicals contain 1 to 7 carbon atoms.

8. A display according to claim 1, wherein component A further comprises one or more compounds of the formula T3a

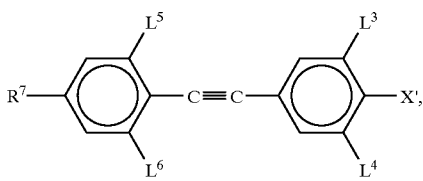

T3a in which $R^7$ is —$C_xH_{2x+1}$, —$OC_xH_{2x+1}$,

[structure: $C_xH_{2x+1}$—cyclohexyl—]  or

[structure: $C_xH_{2x+1}$—cyclohexyl—$CH_2CH_2$—], x is an integer from 1 to 15, $L^{3-6}$ are each, independently of one another, H or F, and X' is F, Cl or $OCF_3$.

9. A display according to claim 1, wherein component B comprises at least one compound of the formula IA or of the formula IB

[structure IA: $R^a$—CH=CH—H(cyclohexyl)—phenyl—phenyl—R]

[structure IB: $R^b$—CH=CH—CH$_2$—H(cyclohexyl)—phenyl—phenyl—R]

in which

R is as defined, $R^a$ is H or an alkyl radical having 1 to 5 carbon atoms, and $R^b$ is H or an alkyl radical having 1 to 3 carbon atoms.

10. A nematic liquid-crystal mixture comprising a) 10–65% by weight of a liquid-crystalline component A consisting of one or more compounds having a dielectric anisotropy of greater than +1.5;

b) 20–90% by weight of a liquid-crystalline component B consisting of one or more compounds having a dielectric anisotropy of between −1.5 and +1.5;

c) 0–20% by weight of a liquid-crystalline component D consisting of one or more compounds having a dielectric anisotropy of below −1.5, and d) an optically active component C in such an amount that the ratio between the layer thickness of the separation of the plane-parallel outer plates and the natural pitch of the chiral nematic liquid-crystal mixture is from about 0.2 to 1.3, wherein component B comprises at least one compound of the formula I

[structure I: Alkenyl—H(cyclohexyl)—phenyl—phenyl—R]

and component A comprises at least one compound of the formula I'

[structure I': R—[H(cyclohexyl)]$_b$—phenyl—COO—phenyl(F, CN, $L^2$)]

in which alkenyl is an alkenyl radical having 2 to 7 carbon atoms,

R is an alkyl group having 1 to 12 carbon atoms, in which, in addition, one or two non-adjacent $CH_2$ groups are optionally replaced by —O—, —CH=CH—, —CO—, —OCO— or —COO—, b is 0 or 1, and $L^2$ is H or F.

11. A mixture according to claim 10, wherein component A further comprises a compound of the formulae II, II' or III

[structure II: R—[A]$_a$—$Z^1$—phenyl($L^1$, CN, $L^2$)]

[structure II': R—[A]$_a$—COO—phenyl—CN]

[structure III: R—[B]$_b$—C—$Z^2$—phenyl($L^3$, Q—Y, $L^4$)]

in which

R is an alkyl group having 1 to 12 carbon atoms, in which, in addition, one or two non-adjacent $CH_2$ groups are optionally replaced by —O—, —CH=CH—, —CO—, —OCO— or —COO—,

[structures: A (cyclohexyl), B (cyclohexyl) and C (cyclohexyl)]

are each, independently of one another,

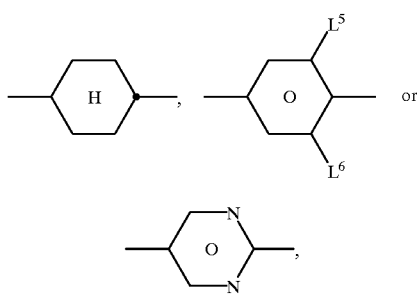

$L^{1-6}$ are each, independently of one another, H or F,
$Z^1$ is —CH$_2$CH$_2$— or a single bond,
$Z^2$ is —CH$_2$CH$_2$—, —COO—, —C≡C— or a single bond,
Q is —CF$_2$—, —CHF—, —OCF$_2$—, —OCFH— or a single bond,
Y is F or Cl,
a is 1 or 2, and
b is 0 or 1.

12. A mixture according to claim 10, wherein component A further comprises at least one compound selected from the formulae IIa to IIc and II'a

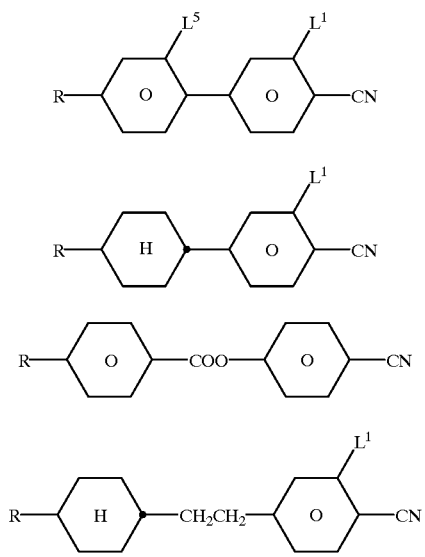

in which
R is an alkyl group having 1 to 12 carbon atoms, in which, in addition, one or two non-adjacent CH$_2$ groups are optionally replaced by —O—, —CH=CH—, —CO—, —OCO— or —COO—, and
$L^1$ and $L^5$ are independently H or F.

13. A mixture according to claim 10, wherein component B further comprises one or more compounds of the following formulae

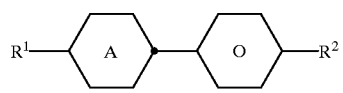

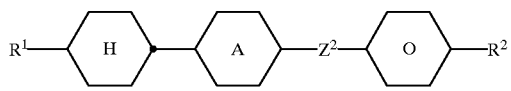

in which
$R^1$ and $R^2$ are each, independently of one another, alkyl, alkoxy, alkenyl or alkenyloxy having 1–12 carbon atoms,

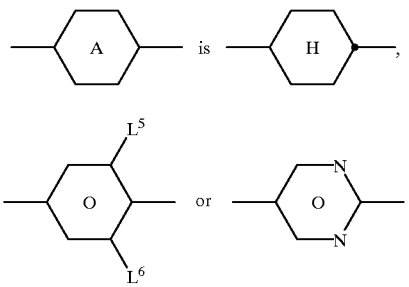

$L^5$ and $L^6$ are each, independently of one another, H or F, and
$Z^2$ is —CH$_2$CH$_2$—, —COO—, —C≡C— or a single bond, where, in the compounds R

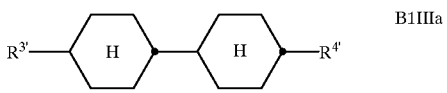

in which $Z^2$ is a single bond, is 1,4-phenylene and $R^1$ is an alkenyl group having 1 to 12 carbon atoms, at least one of the 1,4-phenylene groups must be at least monosubstituted by fluorine.

14. A mixture according to claim 10, wherein the liquid crystal mixture comprises one or more compounds of formula B1IIIa in which
$R^{3'}$ is CH$_3$—(CH$_2$)$_o$—O—, CH$_3$—(CH$_2$)$_p$—, trans-H—(CH$_2$)$_q$—CH=CH—(CH$_2$CH$_2$)$_b$—CH$_2$O—, trans-H—(CH$_2$)$_q$—CH=CH—(CH$_2$CH$_2$)$_b$—, or CH$_3$—(CH$_2$)$_o$—O—CH$_2$—,
$R^{4'}$ is CH$_3$—(CH$_2$)$_p$—,
o is 1, 2, 3 or 4,
q is 0, 1, 2 or 3,
b is 0 or 1, and
p is 1, 2, 3 or 4.

15. A mixture according to claim 10, wherein component D comprises one or more compounds selected from the group consisting of those of the formulae V to IX

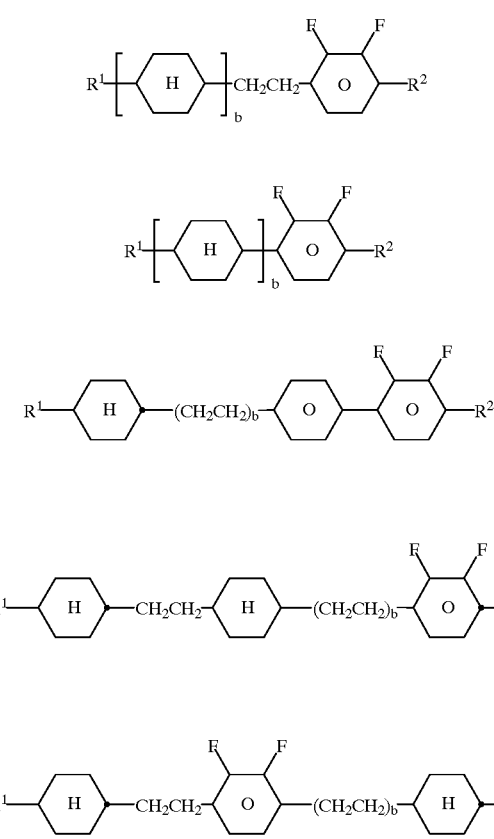

in which $R^1$ and $R^2$ are as defined for R and b is 0 or 1.

16. A mixture according to claim 10, wherein component B further comprises one or more compounds selected from the group consisting of those of the formulae Xa to XIIa

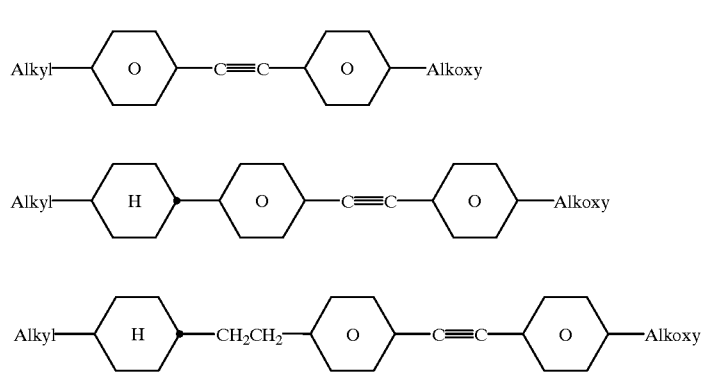

in which the alkyl and alkoxy radicals contain 1 to 7 carbon atoms.

17. A mixture according to claim 10, wherein component A further comprises one or more compounds of the formula T3a

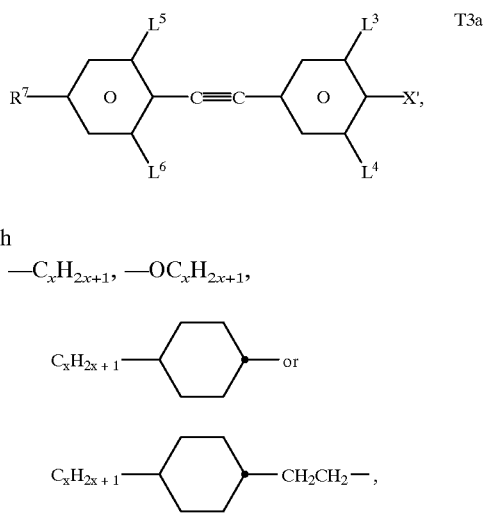

in which
$R^7$ is $—C_xH_{2x+1}$, $—OC_xH_{2x+1}$, x is an integer from 1 to 15,
$L^{3-6}$ are each, independently of one another, H or F, and
X' is F, Cl or $OCF_3$.

18. A mixture according to claim 10, wherein component B comprises at least one compound of the formula IA or of the formula IB

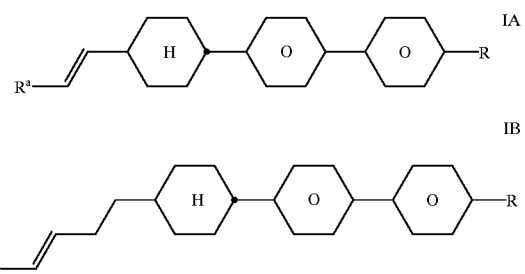

in which

R is as defined,
$R^a$ is H or an alkyl radical having 1 to 5 carbon atoms, and
$R^b$ is H or an alkyl radical having 1 to 3 carbon atoms.

* * * * *